Figure 1:
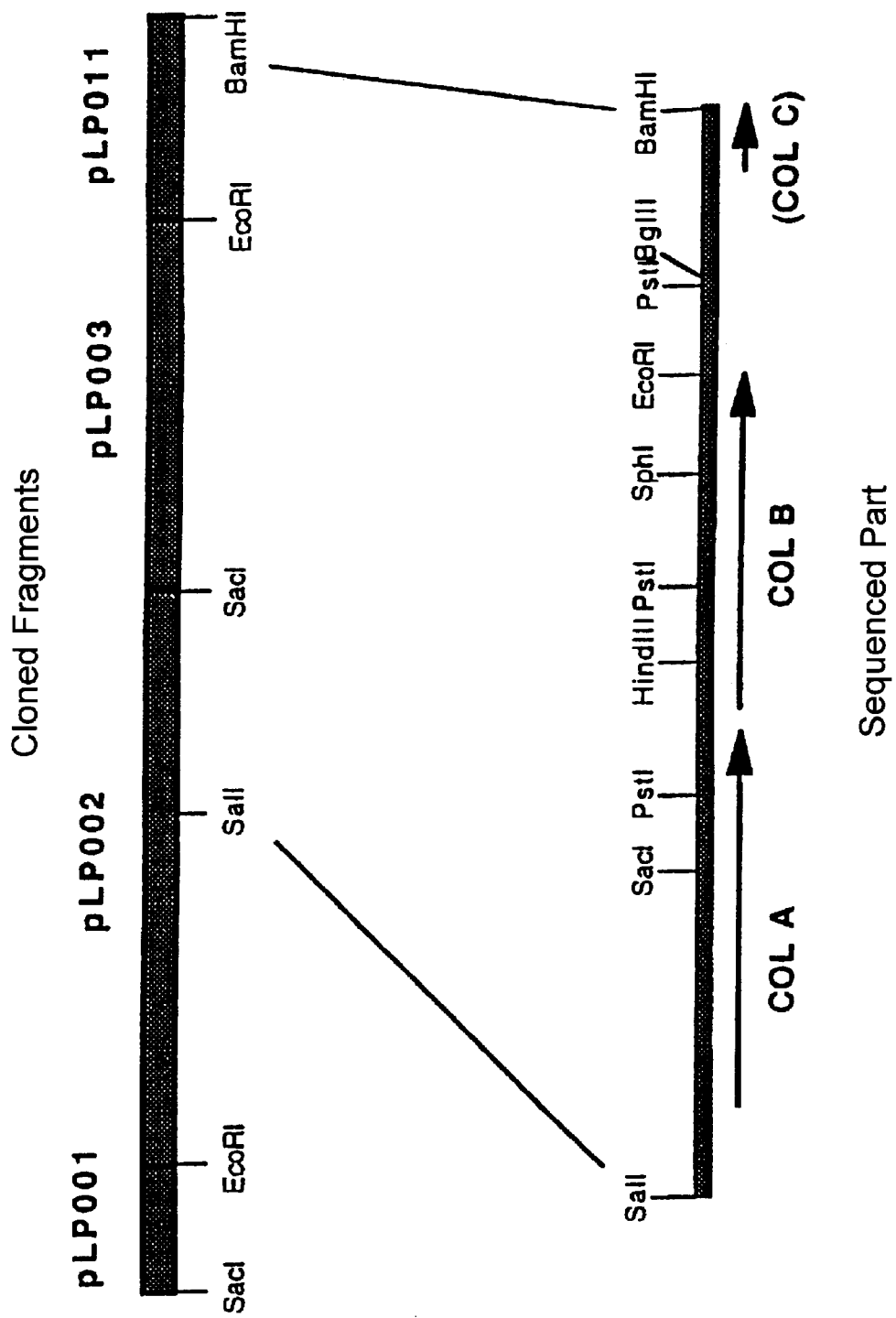

United States Patent [19]
Audonnet et al.

[11] Patent Number: 6,153,199
[45] Date of Patent: Nov. 28, 2000

[54] AVIAN RECOMBINANT LIVE VACCINE USING, AS VECTOR, THE AVIAN INFECTIOUS LARYNGOTRACHEITIS VIRUS

[75] Inventors: Jean-Christophe Audonnet, Lyons; Michel Bublot, Les Olieres; Michel Riviere, Ecully, all of France

[73] Assignee: Merial, Lyons, France

[21] Appl. No.: 09/219,932

[22] Filed: Dec. 23, 1998

Related U.S. Application Data

[63] Continuation of application No. PCT/FR97/01138, Jun. 25, 1997.

[30] Foreign Application Priority Data

Jun. 27, 1996 [FR] France ................................. 96 08243

[51] Int. Cl.[7] .............................. A61K 39/12; C12N 7/01; C12N 15/38; C12N 15/86
[52] U.S. Cl. ..................................... 424/199.1; 435/235.1; 435/320.1; 424/229.1; 424/816; 424/93.2
[58] Field of Search ...................... 536/23.72; 424/199.1, 424/229.1, 43.2, 816; 435/320.1, 235.1

[56] References Cited

U.S. PATENT DOCUMENTS 5,733,554  3/1998  Audonnet et al. .

FOREIGN PATENT DOCUMENTS

| WO 90/02803 | 3/1990 | WIPO . |
| WO 92/03554 | 3/1992 | WIPO . |
| WO 93/25655 | 12/1993 | WIPO . |
| WO 96/00791 | 1/1996 | WIPO . |
| WO 96/29396 | 9/1996 | WIPO . |

OTHER PUBLICATIONS

Kingsley et al, Virology 203:336–343, 1994.
Wilson et al, Virology 199:393–402, 1994.
A.M. Griffin, "Identification of 21 Genes of Infectious Laryngotracheitis Virus Using Random Sequencing of Genomic DNA", J. Gen Viro 1, vol. 70 (1989) pp. 3085–3089.
M.A. Johnson, et al, "Gallid Herpesvirus 1 (Infectious Laryngotracheitis Virus): Cloning and Physical Maps of the SA–2 Strain", Archives of Virology, vol. 119 (1991) pp. 181–198.
Martha A. Wild, et al, "A Genomic Map of Infectious Laryngotracheitis Virus and The Sequence and Organization of Genes Present In The Unique Short and Flanking Regions", Virus Genes, vol. 12:2 (1996) pp. 107–116.

Primary Examiner—Mary E. Mosher
Attorney, Agent, or Firm—Frommer Lawrence & Haug LLP; William S. Frommer; Thomas J. Kowalski

[57] ABSTRACT

The living recombinant avian vaccine comprises, as a vector, an ILTV virus comprising and expressing at least one heterologous nucleotide sequence, this nucleotide sequence being inserted in the insertion locus defined between the nucleotides 1624 and 3606 at the SEQ ID NO: 5. The vaccine may in particular comprise a sequence coding for an antigen of an avian pathogenic agent selected among the group consisting of the Newcastle disease virus (NDV), the infections bursal virus (IBDV), the Marek disease virus (MDV), the infectious bronchitis virus (IBV), the chicken anaemia virus (CAV), thee chicken pneumovirosis virus, preferably under the control of a strong eukaryotic promoter. A multivalent vaccine formula is also disclosed.

46 Claims, 24 Drawing Sheets

```
                    SalI
   1  GTCGACTGCCAGTGGAAGATAAAATCCCTTCTCAATTTTTAACGATAAATGAACACTGAG
  61  TCCATGGTTTCGAATAAAGCGACGCATTCCCAAGATTCCCATATCGGTATATTTCGAGGA
 121  GAGCAAATGAAAAGACAGAAGCCCGCAAGTCTCGTATCAGCAAACTAATATTTAGGGCGC
 181  TCTGAAAGGCGGTATTTGTATGTACAGGGGTTGGGCAATCCACACCCTCGTAATCGCATT
 241  ACACATAAGGTGTGACATGGTGGTAGCCCCAAAATTTTATGCACAGGCTACAGTTGTATA
                         ORF A --->
 301  TAAACCGCGCGGATGTTTAGGAGATGTTCAGAGACACCGGGGGAGGGAACGAACGTACAC
                1▶ Met Phe ArgArgCysSer GluThr ProGlyGluGlyThrAsnValHis
 361  ACGAATTACGTTCGTTGGAAGATGGATTTGGATACTGCGACAAGAAGTAAATGTTTGCTC
        17▶ ThrAsnTyrValArgTrpLysMetAspLeuAspThrAlaThrArgSerLysCysLeuLeu
 421  CGACTAACTTTAGGAAAGCATGGGATTTCGGTGGTTTCCCCCATTGCCAAAAACATGCGT
        37▶ ArgLeuThrLeuGlyLysHisGlyIleSerValValSerProIleAlaLysAsnMetArg
 481  GGGATTCTGCAACACTCTGTGCTGGCTTTTATGAATGACTGCATAGTAATTTCCTGTTCC
        57▶ GlyIleLeuGlnHisSerValLeuAlaPheMetAsnAspCysIleValIleSerCysSer
 541  GCTCCGTTTGGGATGGCTTTCTTAAAAATCAAGTGGCAATTGTTCGACTCATTTGAATAT
        77▶ AlaProPheGlyMetAlaPheLeuLysIleLysTrpGlnLeuPheAspSerPheGluTyr
 601  TTATCAGACGATGAGAGTATACTACCTATCATGCTCAATAATACTATACACCAGCGCCCT
        97▶ LeuSerAspAspGluSerIleLeuProIleMetLeuAsnAsnThrIleHisGlnArgPro
 661  GGAGACCTCTTGGATTTTCTGTGGGACTCTAAGAAAAAAACTGTCGGAATACCAACTTTA
       117▶ GlyAspLeuLeuAspPheLeuTrpAspSerLysLysLysThrValGlyIleProThrLeu
 721  GCCACATTTACTATATCAGAAAGTTTCAAATCCGATGAAACTAGGGCTGTACACAGACTG
       137▶ AlaThrPheThrIleSerGluSerPheLysSerAspGluThrArgAlaValHisArgLeu
 781  AAAGTCTGTCGCGAGATAGAAGAGAGCGCGTCGTGCCCCAAAATACGGAAATAAGCACG
       157▶ LysValCysArgGluIleGluGluSerAlaSerCysProGlnAsnThrGluIleSerThr
 841  AAAATTCAAGTACTCTTCATCGGATGGACCTCCTATATACCTGCCTCGTTCCGATAAGCA
       177▶ LysPheLysTyrSerSerSerAspGlyProProIleTyrLeuProArgSerAspLysAla
 901  TGTCGGGCCTCGCTGGAACAGTATTCGTTCAATGAAATTACAAAGTGGCTTTCGAAGATC
       197▶ CysArgAlaSerLeuGluGlnTyrSerPheAsnGluIleThrLysTrpLeuSerLysIle
 961  CCTAAAGATAACTCAATTACAGTCACACTCACAAGAGAGTATGTCACGTTCTCGTCCGCA
       217▶ ProLysAspAsnSerIleThrValThrLeuThrArgGluTyrValThrPheSerSerAla
1021  GAAGACGAGCAACGCCTAACCTTTAACGCGAAATGGTTCGGCGACCAGACAAGTATTGTA
       237▶ GluAspGluGlnArgLeuThrPheAsnAlaLysTrpPheGlyAspGlnThrSerIleVal
                                                              SacI
1081  TCGTCTGCGTCAATTTTGTCTCAGCTATGTGGCCATGAACCTGCGCCTAAAAAAAGAGAG
       257▶ SerSerAlaSerIleLeuSerGlnLeuCysGlyHisGluProAlaProLysLysArgGlu
1141  CTCTCAAGCCGAGCCATCGGTAAGAAACTAAAAGAAGCCCGCCATTATCGCTGTTCATGG
       277▶ LeuSerSerArgAlaIleGlyLysLysLeuLysGluAlaArgHisTyrArgCysSerTrp
1201  GGACAAAGATGCCTGCCCCATTGTAGTATCACTCTCCAGACCCGGATCTCTGAAACAGTC
       297▶ GlyGlnArgCysLeuProHisCysSerIleThrLeuGlnThrArgIleSerGluThrVal
1261  ACTAGGGTGGCTGAAAAGCGGTCCTTGGGGACACCGTGTCTTACATTTTACAAAGACTCT
       317▶ ThrArgValAlaGluLysArgSerLeuGlyThrProCysLeuThrPheTyrLysAspSer
1321  GTGAATAGTCTTGGAGTAGAACTCTCTGAAAGAGGAGGAGAAGAATTAGCTGCTGGGATT
       337▶ ValAsnSerLeuGlyValGluLeuSerGluArgGlyGlyGluGluLeuAlaAlaGlyIle
                     PstI
1381  TTTTTCCTTTCCGCGTTTTCTGCAGATGGAGCAATCTCTGAGCAATGCCATGATGACTCA
       357▶ PhePheLeuSerAlaPheSerAlaAspGlyAlaIleSerGluGlnCysHisAspAspSer
1441  GACACAGCCATGCACGAATTTTTGGCGGAGGAGGAGCGCCTCATACAACAGACCACGCTA
       377▶ AspThrAlaMetHisGluPheLeuAlaGluGluGluArgLeuIleGlnGlnThrThrLeu
1501  TCCCATTCCAACTCAAGTAAGAAGAGGTCGCTCGAAAATTACGAGGACACCGATATTAGC
       397▶ SerHisSerAsnSerSerLysLysArgSerLeuGluAsnTyrGluAspThrAspIleSer
1561  CCATCCCACCACCCACAAAAGCGGGGGAAATTAAAGAACGGCTCACTTGCACGGAAGAAC
       417▶ ProSerHisHisProGlnLysArgGlyLysLeuLysAsnGlySerLeuAlaArgLysAsn
1621  TAAAATCGTCTCCTCGCGTCTACCGGGGAGCTTAGTTTACTGCCAGCGTTTGTGACCCAA
       437▶ ...
                                               ORF B --->
1681  GTGTGCACCGTGATTTCAACTCTACCGCAACTATGACGGGGGCTACCATAATTGATCCAT
                                      1▶ MetThrGlyAlaThrIleIleAspProP
```

FIG 2

```
1741 TCGCACCGCCCAAGGGTAAATGGTGGCCGTTCAATTTGAACGGGATAGTTTTTTCCTTGA
  10▶ heAlaProProLysGlyLysTrpTrpProPheAsnLeuAsnGlyIleValPheSerLeuM
1801 TGATGTTTATTATATTTTTAGCCTGGATACTGCGCATTGACTATGGACTCGCGTTAGCTT
  30▶ etMetPheIleIlePheLeuAlaTrpIleLeuArgIleAspTyrGlyLeuAlaLeuAlaT
                                                              HindIII
1861 ACATTACCTGGGCAAAGCTTTCTACGAAAGAGGCAAGATTCGGATGGATGATCGGACTAT
  50▶ yrIleThrTrpAlaLysLeuSerThrLysGluAlaArgPheGlyTrpMetIleGlyLeuL
1921 TGGTGGCTACGATTACTGCCAGTTTTCTGGATATTCAATACTCGGCTCACAAAACAGTCC
  70▶ euValAlaThrIleThrAlaSerPheLeuAspIleGlnTyrSerAlaHisLysThrValA
1981 GAATTTATTTTCTGGTGATGCTTTCTATGGCGAGCGCAGTAATAATTATATTTCTCATCC
  90▶ rgIleTyrPheLeuValMetLeuSerMetAlaSerAlaValIleIleIlePheLeuIleH
2041 ATTCCAACAGCCCCAATGCCGCGATAGTTATGGGGCTATTCTCCGTTTTTTCGGAAGTTT
 110▶ isSerAsnSerProAsnAlaAlaIleValMetGlyLeuPheSerValPheSerGluValC
                                                              PstI
2101 GCTTGATACTGATTTTGGGATTTCAACTCCGACCGGCCATTTTCTGCAGCATAAACATGA
 130▶ ysLeuIleLeuIleLeuGlyPheGlnLeuArgProAlaIlePheCysSerIleAsnMetT
2161 CCTGGCTCTTTCTTGAAGCCATGCTCCTAAATTTGACCGTACTTTCTTGGAACTTGATGC
 150▶ hrTrpLeuPheLeuGluAlaMetLeuLeuAsnLeuThrValLeuSerTrpAsnLeuMetH
2221 ACCTTCGAGTAAACCCTAGATACTTGGAACCGTTGGCCCTTTTTACTATTAACATTTTGG
 170▶ isLeuArgValAsnProArgTyrLeuGluProLeuAlaLeuPheThrIleAsnIleLeuA
2281 CATACAATCCCTCTCGTTTTTTGCTCAAGAGTGATTTTTTTAAGACCAGCATGATAACTC
 190▶ laTyrAsnProSerArgPheLeuLeuLysSerAspPhePheLysThrSerMetIleThrL
2341 TGACGGGCAGTATAGAACCATTTTCCGAAGATAACACGATTTATACACCCCCAAGACAAC
 210▶ euThrGlySerIleGluProPheSerGluAspAsnThrIleTyrThrProProArgGlnH
2401 ATAAAGATACTCGCCCTTCACTGAATGACGGACCAACTCGGTGGTGCGGTTACTGTATTC
 230▶ isLysAspThrArgProSerLeuAsnAspGlyProThrArgTrpCysGlyTyrCysIleL
2461 TCGTATCTACAACATTGGTTACTGCCGCTTTCGCCTGCACATTATCATTACCGTTCCTGG
 250▶ euValSerThrThrLeuValThrAlaAlaPheAlaCysThrLeuSerLeuProPheLeuG
                                                              SphI
2521 GCAAAGATTTAGGTACTGTACGCATCGGCATGCAAACGAATTTTAAAATCCTCATGGTAG
 270▶ lyLysAspLeuGlyThrValArgIleGlyMetGlnThrAsnPheLysIleLeuMetValA
2581 CGTGCGGTTCGGTTTTGGCATTTGGATCTACTTGCATTGGAAAACTATGCAAAATCCATA
 290▶ laCysGlySerValLeuAlaPheGlySerThrCysIleGlyLysLeuCysLysIleHisI
2641 TCGTTGTATGGTTCGTGATAAGCATACTATTAACCTTCGTGTCTCTGCTATCACTGATTA
 310▶ leValValTrpPheValIleSerIleLeuLeuThrPheValSerLeuLeuSerLeuIleL
2701 AGTTGATTGAGGACCCAGCTGACATTCCATTTGGTGTCATTCTTGCATCGGTTTCTTGTC
 330▶ ysLeuIleGluAspProAlaAspIleProPheGlyValIleLeuAlaSerValSerCysL
2761 TGTTTCAAGTTGGAGCCCTCTTTTTCCGAGAATTAAAAACGGCCACCCATACACAAGGAT
 350▶ euPheGlnValGlyAlaLeuPhePheArgGluLeuLysThrAlaThrHisThrGlnGlyT
2821 GGATTTCATGCGCCCTTCTTTTCTGCTCCCTTTTCATTCCAATTGCCGCGCCGCTTGTGT
 370▶ rpIleSerCysAlaLeuLeuPheCysSerLeuPheIleProIleAlaAlaProLeuValC
                                                              EcoRI
2881 GTGAGTACAAGCTCTGAATTCTTGTCTAAGGGAGACGTGCCAATTCTGACAACGCCCTAA
 390▶ ysGluTyrLysLeu• • •
2941 GCCAACACAAATGCCTTCCTCAATTTACGCGCTAGCTTGAACATTCCAACAAGATGAATG
3001 CATCGCTAACATGGCTTGCTTTAACTTTTAAAGTTACCTTGAGTTTCAGCCTGCTCTGAA
3061 TGTTTTCCTCCAAACCTAAGATGTTCTTAGTTGTACGATTTTTGTATTGCGAATACCACA
3121 TCATCCAGTACCAAAGTACTAATGGTCGGCAATCGAATAGAAATCAAACATGGCACGCAG
                                                              PstI
3181 GAGACTGTCGCCTCGAAACTGCCTTCGCCGAGCTGCAGAAATTCGGAACGAGGACATTAG
                                                              BglII
3241 AAACAGATCTACATTCCACCGAGCAACCGTTTACTGGAGAAAATGCTAGAGAATAACCTA
3301 ACAGGCGGCCTTCAACTTTCACTACTTAACAACTGGAACTATATTGTCGAGGATTGTCAT
3361 AGTCACGAACATGATGCAGTATTGCTTCGGATGCAATCTATATTTTGACATTGTTAATAA
3421 AGCACATGTACTATGCAAAGTTTGCATTCGTGTAATTCGTCGAGGAGAGAAAGTTACAAGT
3481 TCGATTCTCTCGCGCTAGGAGTGTTTCCACGTGCGAAAACGCAAAAATTTTCATATTATT
3541 CGGGCGGACTGTGTCCATAGTAGCTAAATTACCGCGATCTGGAGACTAGGGCATTCACGA
              ORF C --->
3601 CTCAACATGCAGCATCAGAGTACTGCGCTAGTTTCGAGTATACTTTTGCTCTTGAGCCTG
   1▶ MetGlnHisGlnSerThrAlaLeuValSerSerIleLeuLeuLeuLeuSerLeu
3661 CAAAGCCTTGCGTTTGAATTTTTCTGTGATCCGCCACACGTTTTTCGAGGGCAGCTCGGT
  19▶ GlnSerLeuAlaPheGluPhePheCysAspProProHisValPheArgGlyGlnLeuGl;
3721 GACCCCATTCTATTGCAATGCTTCAGCGACAGACCTCTAACCCACGAAGAATCTGTAAAA
  39▶ AspProIleLeuLeuGlnCysPheSerAspArgProLeuThrHisGluGluSerValLys
```

FIG 2 (continued)

```
                                                                    BamHI
3781 GTAGAAGTAATTCGACACCCAGCCAGCTTAGTTGAAACTGCGCTAAGCGCCTACGGGATC
  59▶ ValGluValIleArgHisProAlaSerLeuValGluThrAlaLeuSerAlaTyrGlyIle
3841 C
  79▶
```

FIG 2 (continued)

```
   1 TGCTACCTGATGTACAAGCAAAAGGCACAACAAAAGACCTTGTTATGGCTTGGGAATAAT
  61 ACCCTTGATCAGATGAGAGCCACTACAAAAATATGAATACAAACGAGAGGCGGAGGTATC
 121 CCCAATAGCAATTTGCGTGTAAATTCTGGCAACCTGTTAATTAGAAGAATTAAGAAAAAA
 181 CCACTGGATGTAAGTGACAAACAAGCAATACACGGGTAGAACGGTCGGAGAAGCCACCCC
 241 TCAATCGGGAATCAGGCCTCACAACGTCCTTTCTACCGCATCATCAATAGCAGACTTCGG
 301 TCATGGACCGTGCAGTTAGCAGAGTTGCGCTAGAGAATGAAGAAAGAGAAGCAAAGAATA
     1▶MetAspArgAlaValSerArgValAlaLeuGluAsnGluGluArgGluAlaLysAsnT
 361 CATGGCGTTTGTATTCCGGATTGCAATCTTACTTTTAATAGTAACAACCTTAGCCATCT
    20▶hrTrpArgPheValPheArgIleAlaIleLeuLeuLeuIleValThrThrLeuAlaIleS
 421 CTGCAACCGCCCTGGTATATAGCATGGAGGCTAGCACGCCTGGCGACCTTGTTGGCATAC
    40▶erAlaThrAlaLeuValTyrSerMetGluAlaSerThrProGlyAspLeuValGlyIleP
 481 CGACTATGATCTCTAAGGCAGAAGAAAAGATTACATCTGCACTCAGTTCTAATCAAGATG
    60▶roThrMetIleSerLysAlaGluGluLysIleThrSerAlaLeuSerSerAsnGlnAspV
 541 TAGTAGATAGGATATATAAGCAGGTGGCCCTTGAGTCTCCATTGGCGTTGCTAAACACTG
    80▶alValAspArgIleTyrLysGlnValAlaLeuGluSerProLeuAlaLeuLeuAsnThrG
 601 AATCTGTAATTATGAATGCAATAACGTCTCTCTCTTATCAAATCAATGGAGCTGCAAATA
   100▶luSerValIleMetAsnAlaIleThrSerLeuSerTyrGlnIleAsnGlyAlaAlaAsnA
                                                          BspHI
 661 ATAGCGGGTGTGGGGCACCTGTTCATGACCCAGATTATATCGGGGGGATAGGCAAAGAAC
   120▶snSerGlyCysGlyAlaProValHisAspProAspTyrIleGlyGlyIleGlyLysGluL
 721 TTATTGTGGATGACGCTAGTGATGTACATCATTCTATCCCTCTGCGTTCCAAGAACACC
   140▶euIleValAspAspAlaSerAspValThrSerPheTyrProSerAlaPheGlnGluHisL
 781 TGAACTTTATCCCGGCACCTACTACAGGATCAGGTTGCACTCGGATACCCTCATTCGACA
   160▶euAsnPheIleProAlaProThrThrGlySerGlyCysThrArgIleProSerPheAspI
 841 TAAGCGCTACCCACTACTGTTACACTCACAATGTGATATTATCTGGTTGCAGAGATCACT
   180▶leSerAlaThrHisTyrCysTyrThrHisAsnValIleLeuSerGlyCysArgAspHisS
 901 CACACTCATATCAGTACTTAGCACTTGGCGTGCTTCGGACATCTGCAACAGGGAGGGTAT
   200▶erHisSerTyrGlnTyrLeuAlaLeuGlyValLeuArgThrSerAlaThrGlyArgValP
 961 TCTTTTCTACTCTGCGTTCCATCAATTTGGATGACAGCCAAAATCGGAAGTCTTGCAGTG
   220▶hePheSerThrLeuArgSerIleAsnLeuAspAspSerGlnAsnArgLysSerCysSerV
1021 TGAGTGCAACTCCCTTAGGTTGTGATATGCTGTGCTCTAAAATCACAGAGACTGAGGAAG
   240▶alSerAlaThrProLeuGlyCysAspMetLeuCysSerLysIleThrGluThrGluGluG
                                                          ClaI
1081 AGGATTATAGTTCAATTACGCCTACATCGATGGTGCACGGAAGGTTAGGGTTTGACGGTC
   260▶luAspTyrSerSerIleThrProThrSerMetValHisGlyArgLeuGlyPheAspGlyG
1141 AATACCATGAGAAGGACTTAGACGTCATAACTTTATTTAAGGATTGGGTGGCAAATTACC
   280▶lnTyrHisGluLysAspLeuAspValIleThrLeuPheLysAspTrpValAlaAsnTyrP
1201 CAGGAGTGGGGGGTGGGTCTTTTATTAACAACCGCGTATGGTTCCCAGTCTACGGAGGGC
   300▶roGlyValGlyGlyGlySerPheIleAsnAsnArgValTrpPheProValTyrGlyGlyL
1261 TAAAACCCAATTCGCCTAGTGACACCGCACAAGAAGGGAGATATGTAATATACAAGCGCT
   320▶euLysProAsnSerProSerAspThrAlaGlnGluGlyArgTyrValIleTyrLysArgT
1321 ACAATGACACATGCCCAGATGAACAAGATTACCAGATTCGGATGGCTAAGTCTTCATATA
   340▶yrAsnAspThrCysProAspGluGlnAspTyrGlnIleArgMetAlaLysSerSerTyrL
1381 AGCCTGGCGGTTTGGTGGAAAACGCGTACAGCAGGCCATCTTATCTATCAAGGTGTCAA
   360▶ysProGlyArgPheGlyGlyLysArgValGlnGlnAlaIleLeuSerIleLysValSerT
1441 CATCTTTGGGCGAGGACCCGGTGCTGACTGTACCGCCTAATACAATCACACTCATGGGGG
   380▶hrSerLeuGlyGluAspProValLeuThrValProProAsnThrIleThrLeuMetGlyA
1501 CCGAACGGAGAGTTCTCACAGTAGGGACATCTCATTTCTTGTACCAGCGAGGGTCTTCAT
   400▶laGluArgArgValLeuThrValGlyThrSerHisPheLeuTyrGlnArgGlySerSerT
```

FIG 14   Sequence of the NDV HN gene

1561 ACTTCTCTCCTGCTTTATTATACCCTATGACAGTCAACAACAAAACGGCTACTCTTCATA
420▶yrPheSerProAlaLeuLeuTyrProMetThrValAsnAsnLysThrAlaThrLeuHisS
1621 GTCCTTACACATTCAATGCTTTCACTAGGCCAGGTAGTGTCCCTTGTCAGGCATCAGCAA
440▶erProTyrThrPheAsnAlaPheThrArgProGlySerValProCysGlnAlaSerAlaA
1681 GATGCCCCAACTCATGTGTCACTGGAGTTTATACTGATCCGTATCCCTTAGTCTTCCATA
460▶rgCysProAsnSerCysValThrGlyValTyrThrAspProTyrProLeuValPheHisA
1741 GGAACCATACCTTGCGGGGGGTATTCGGGACAATGCTTGATGATGAACAAGCAAGACTTA
480▶rgAsnHisThrLeuArgGlyValPheGlyThrMetLeuAspAspGluGlnAlaArgLeuA
                             PstI
1801 ACCCTGTATCTGCAGTATTTGATAACATATCCCGCAGTCGCATAACCCGGGTAAGTTCAA
500▶snProValSerAlaValPheAspAsnIleSerArgSerArgIleThrArgValSerSerS
1861 GCCGTACTAAGGCAGCATACACGACATCGACATGTTTTAAAGTTGTCAAGACCAATAAAA
520▶erArgThrLysAlaAlaTyrThrThrSerThrCysPheLysValValLysThrAsnLysT
1921 CATATTGCCTCAGCATTGCAGAAATATCCAATACCCTCTTCGGGGAATTCAGGATCGTTC
540▶hrTyrCysLeuSerIleAlaGluIleSerAsnThrLeuPheGlyGluPheArgIleValP
1981 CTTTACTAGTTGAGATTCTCAAGGATGATGGGATTTAAGAAGCCAGGTCTGGCCAGTTGA
560▶roLeuLeuValGluIleLeuLysAsp
2041 GTCAACTGCGAGAGGGTCGGAAAGATGACATTGTGTCACCTTTTTTTGTAATGCCAAGG
2101 ATCAAACTGGATACCGGCGCGAGCCCGAATCCTATGCTGCCAGTCAGCCATAATCAGATA.
2161 GTACTAATATGATTAGTCTTAATCTTGTCGATAGTAACTTGGTTAAGAAAAAATATGAGT
2221 GGTAGTGAGATACACAGCTAAACAACTCACGAGAGATAGCACGGGTAGGACATGGCGAGC
2281 TCCGGTCCCGAAAGGGCAGAGCATCAGATTATCCTACCAGAGTCACATCTGTCCTCACCA
2341 TTGGTCAAGCACAAACTGCTCTATTACTGGAAATTAACTGGCGTACCGCTTCCTGACGAA
2401 TGTGACTTCGACCACCTCATTATCAGCCGACAATGGAAGAAAATACTTGAATCGGCCACT
2461 CCTGACACTGAGAGGATGATAAAGCTCGGGCGGGCAGTACACCAGACTCTCGACCACCGC
2521 C

FIG 14 (continued)

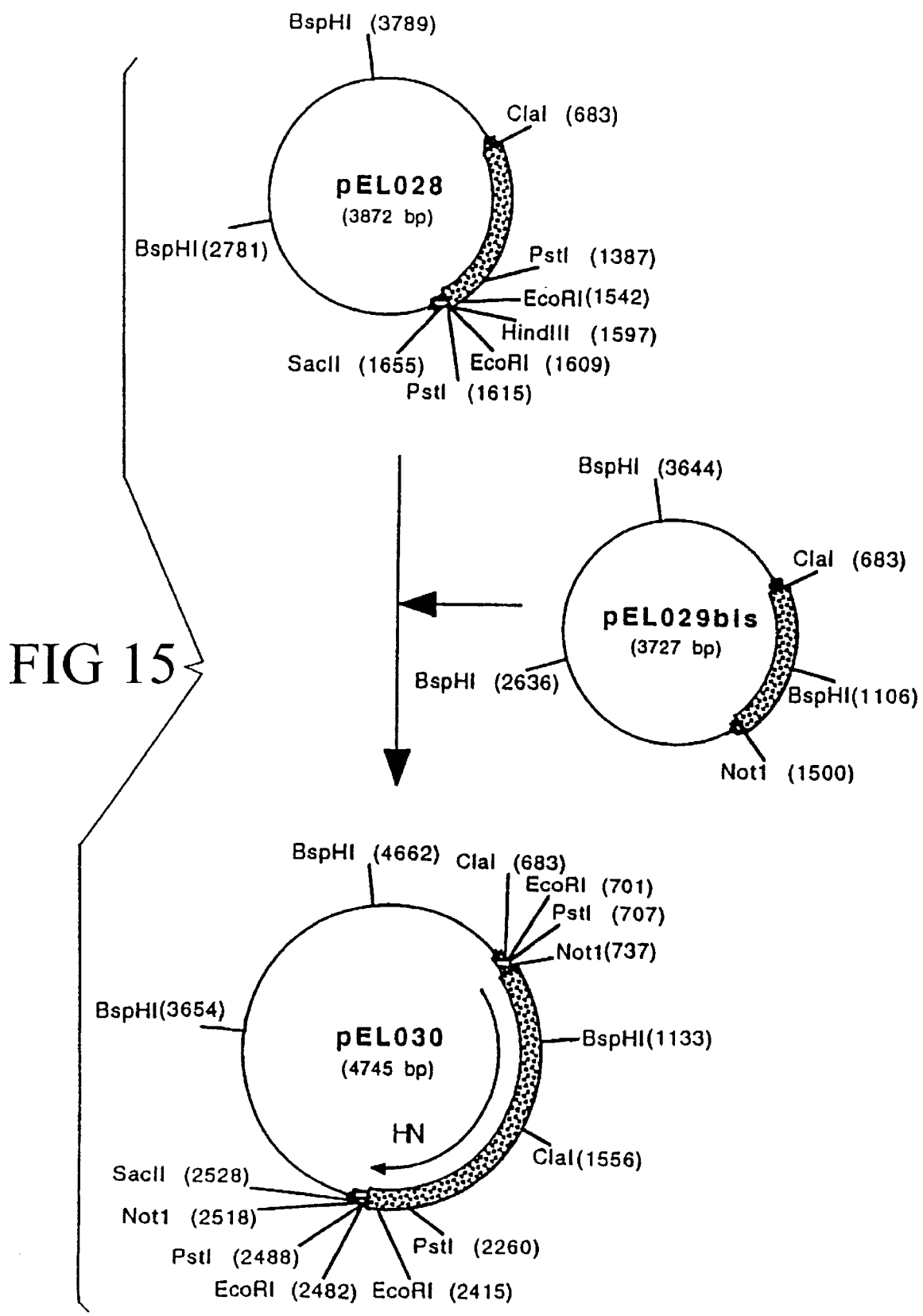

AVIAN RECOMBINANT LIVE VACCINE USING, AS VECTOR, THE AVIAN INFECTIOUS LARYNGOTRACHEITIS VIRUS

This is a continuation of copending International Application PCT/FR97/01138 having an international filing date of Jun. 25, 1997.

The present invention relates to vaccines for avian use based on infectious laryngotracheitis virus (ILTV) into which there has been inserted, by genetic recombination, at least one heterologous nucleotide sequence in particular encoding and expressing an antigenic polypeptide from an avian pathogenic agent, under conditions ensuring immunization leading to effective protection of the vaccinated animal against the said pathogenic agent.

The infectious laryngotracheitis virus (ILTV) is an alpha-herpesvirus (B. Roizman, *Arch. Virol.* 1992. 123. 425–449) which causes a major respiratory pathology (infectious laryngotracheitis or ILT) in chicken (L. E. Hanson and T. J. Bagust, *Diseases of Poultry* 9th edn 1991. pp 485–495. Ames, Iowa State University Press). The vaccines currently available against this condition contain an attenuated strain which can be administered by various routes including the intranasal, conjunctival and cloacal routes, in drinking water and by aerosol (L. E. Hanson and T. J. Bagust, *Diseases of Poultry* 9th Edition 1991. pp 485–495. Ames, Iowa State University Press).

Studies of the molecular biology of the ILTV virus have made it possible to characterize the viral genome (M. A. Johnson et al., *Arch. Virol.* 1991. 119. 181–198) and to identify some of the virus genes (A. M. Griffin, *J. Gen. Virol.* 1989. 70. 3085–3089) including the genes encoding thymidine kinase (UL23) (A. M. Griffin and M. E. G. Boursnell, *J. Gen. Virol.* 1990. 71. 841–850; C. L. Keeler et al., *Avian Dis.* 1991. 35. 920–929), the glycoprotein gB (UL27) (A. M. Griffin, *J. Gen. Virol.* 1991. 72. 393–398; K. Kongsuwan et al., *Virology* 1991. 184. 404–410; D. J. Poulsen et al., *Virus Genes* 1991. 5. 335–347), the glycoprotein gC (UL44) (D. H. Kingsley et al., *Virology* 1994. 203. 336–343), the capsid protein p40 (UL26) (A. M. Griffin, *Nucl. Acids Res.* 1990. 18. 3664), the protein homologous to the ICP4 protein of herpes simplex (HSV-1) (M. A. Johnson et a)., *Virus Research* 1995. 35. 193–204), the proteins homologous to the proteins ICP27 (UL54), glycoprotein gK (UL53) and DNA helicase (UL52) from :HSV-1 (M. A. Johnson et al., *Arch. Virol.* 1995. 140. 623–634), ribonucleotide reductase (A. M. Griffin, *J. Gen. Virol.* 1989. 70. 3085–3089, WO-A-90/02802) the genes present in the short unique sequence of the genome ($U_s$) (M. A. Johnson et al., *DNA Sequence—The Journal of Sequencing and Mapping* 199S. Vol. 5. pp 191–194; K. Kongsuwan et al., *Arch. Virol.* 1995. 140. 27–39; K. Kongsuwan et al., *Virus Research* 1993. 29. 125–140; K. Kongsuwan et al., *Virus Gene* 1993. 7. 297–303; WO-A-92/03554; WO-A-95/00622).

The aim of the present invention is to develop an avian vaccine based on recombinant ILTV virus expressing a heterologous gene, this virus being capable of replicating and inducing immunity in the vaccinated host while preserving good safety.

Another aim of the invention is to provide such a vaccine which is at the same time particularly effective against infectious laryngotracheitis (ILT).

Another aim of the invention is to provide such a vaccine which can be used in mass vaccination by the mucosal route, for example by the aerosol route or in drinking water, such that the replication of the virus at the mucosal level makes it possible to induce mucosal and systemic immunity. Such a mucosal immunity will be particularly effective for combating respiratory diseases as well as other diseases for which the route of entry of the pathogenic agent is mucosal.

Another aim of the invention is to provide such a vaccine which can be used both in adults and in young animals.

A specific aim is to provide such a vaccine which can be used in mass vaccination, by the mucosal route, of any young animals such as one-day old chicks.

Another aim of the invention is to provide a vaccine against ILT which has an increased efficacy compared with the parental strain and which may even possibly allow the insertion and expression of a heterologous gene.

During their studies on the ILTV virus, the inventors found a genomic region which proved entirely appropriate as site for insertion of heterologous genes. This made it possible to develop a recombinant live vaccine based on an ILTV vector into which is inserted at least one sequence encoding an avian immunogen, in particular the HN and F proteins from the Newcastle disease virus (NOV), and/or the gB glycoprotain from Marek's disease virus (MDV), and/or the VP2 protein from the infectious bursal disease virus (IBDV), and/or the S and M proteins from the infectious bronchitis virus (IBV). Such a vaccine, incorporating a sequence encoding NDV, MDV and IBV proteins, provides satisfactory protection of the animals against Newcastle disease, against Marek's disease, against infectious bursal disease and against infectious bronchitis respectively.

The subject of the present invention is therefore an avian recombinant live vaccine comprising, as vector, the ILTV virus comprising at least one heterologous nucleotide sequence in particular encoding and expressing an antigenic polypeptide from an avian pathogenic agent, inserted into the insertion locus which, in a specific ILTV strain, is defined between nucleotides 1624 and 3606 in the sequence SEQ ID No:5.

Heterologous sequence is understood to mean a sequence which is not derived from the insertion locus, that is to say both a sequence not originating from the ILTV virus and a sequence derived from another genomic region of this virus.

Insertion into the insertion region is understood to mean in particular simple insertion or insertion after total or partial deletion of the insertion locus.

There have been determined in this insertion locus an open reading frame (ORF B) which appears between nucleotides 1713 and 2897 in SEQ ID No:5, and an intergenic region (between nucleotides 2898 and 3606) between ORF B and ORF C. It is therefore possible to insert both into ORF B or into the intergenic region, and overlapping these two regions. One or more expression cassettes may be inserted, each comprising at least one sequence to be expressed.

To express the inserted sequence, the use of a strong eukaryotic promoter such as the. CMV immediate early (IE) promoter, the Rous sarcoma virus (RSV) LTR and the SV40 virus early promoter is preferred.

CMV immediate early (IE) promoter is understood to mean the fragment given in the examples as well as its subfragments which retain the same promoter activity.

The CMV IE promoter may be the human promoter (HCMV IE) or the murine promoter (MCMV IE) or alternatively a CMV IE promoter of another origin, for example from monkeys, rats, guinea pigs or pigs.

The nucleotide sequence inserted into the ILTV vector so as to be expressed may be any sequence encoding an antigenic polypeptide, from an avian pathogenic agent, capable, once expressed under the favourable conditions offered by the invention, of providing immunization leading to effective protection of the animal vaccinated against the pathogenic agent. It will therefore be possible to insert, under the conditions of the invention, the nucleotide sequences encoding antigens of interest for a given disease.

This nucleotide sequence inserted into the ILTV vector may also encode an immunomodulatory polypeptide, especially a cytokine.

Remarkably, it will be possible for the vaccines according to the invention to be used for vaccination in ovo of one-day-old or older chicks and of adults. It will be possible to use various routes of administration; the parenteral route, or the mucosal routes such as the oronasal (drinking water, aerosol), conjunctival (eye drop) or cloacal route, with a preference for the routes allowing mass mucosal vaccination (drinking water, aerosol).

The invention proves particularly useful both for protection against respiratory pathologies and against systemic pathologies by blocking the natural routes of entry of the pathogenic agent.

The invention may in particular be used for the insertion of a nucleotide sequence appropriately encoding an antigenic protein from the NDV virus, and in particular the HN glycoprotein or the F glycoprotein. A recombinant live vaccine is thus obtained providing, in addition to protection against infectious laryngotracheitis, satisfactory protection against Newcastle disease.

The recombinant vaccine against Newcastle disease will preferably contain from 10 to 1 PFU/dose.

Other preferred cases of the invention are the insertion of nucleotide sequences encoding antigens from other avian pathogenic agents and in particular, but with no limitation being implied, antigens from Marek's disease, in particular gB, gD and gH+gL genes (WO-A-90/02803), from the infectious bursal disease virus, in particular VP2 gene, from the infectious bronchitis virus (IBV), in particular S and M genes (M. Binns et al., *J. Gen. Virol.* 1985, 66. 719–726; M. Boursnell et al., *Virus Research* 1984. 1. 303–313), from the chicken anaemia virus (CAV), in particular VP1 (52 kDa)+ VP2 (24kDa) (N. H. M. Noteborn et al., *J. Virol.* 1991. 65.3131–3139), from the ILTV virus, in particular the genes coding for gB (A. M. Griffin, *J. Gen. Virol.* 1991. 72. 393–398), or for gD (M. A. Johnson et al., *DNA Sequence— The Journal of Sequencing and Mapping* 1995. Vol. 5. pp 191–194. Harwood Academic Publishers GmbH), or for gp60 (K. K. Kongsuwan et al., *Virus Genes* 1993. 7. 297–303), and from the infectious "swollen head syndrome" virus (or chicken pneumovirosis or turkey rhinotracheitis virus (TRTV); pneumovirus), in particular the fusion glycoprotein F (Q. Yu et al., *J. Gen. Virol.* 1991. 72. 75–81), or the attachment glycoprotein G (R. Ling et al., *J. Gen. Virol.* 1992. 73. 1709–1715; K. Juhasz and J. Easton, *J. Gen. Virol* 1994. 75. 2873–2880). The doses will be preferably the same as those for the Newcastle vaccine.

Within the framework of the present invention, it is of course possible to insert more than one heterologous sequence into the same ILTV virus, in particular into this locus. It is possible in particular to insert therein sequences derived from the same virus or from different viruses, which also comprises the insertion of sequences from ILTV and from another avian virus. It is also possible to associate therewith sequences encoding immunomodulators, and in particular cytokines.

For example, the CMV IE promoter is associated with another promoter so that their 5' ends are adjacent (which implies transcriptions in opposite directions), which makes it possible to insert, into the insertion zone, two nucleotide sequences, one under the control of the CMV IE promoter, the other under that of the associated promoter. This construct is remarkable by the fact that the presence of the CMV IE promoter, and in particular of its activating (enhancer) part, activates the transcription induced by the associated promoter. The associated promoter may be in particular a promoter of a gene from the ILTV virus or from the MDV or HVT virus.

An advantageous case of the invention is a vaccine comprising a nuclectide sequence encoding NDV HN and a nucleotide sequence encoding NDV F or an antigen for another avian disease, especially those mentioned above, one of the genes being under the control of the CMV IE promoter, and the other under the control of the associated promoter.

It is also possible to assemble two CMV IE promoters of different origins with their 5' ends adjacent.

Of course, the heterologous sequences and their associated promoters may be inserted more conventionally in tandem into the insertion locus, that is to say following the same direction of transcription.

The expression of several heterologous genes inserted into the insertion locus may also be possible by insertion of a sequence called "IRES" (Internal Ribosome Entry Site) obtained especially from a picornavirus such as the swine vesicular disease virus (SVDV; B.-F. Chen et al., *J. Virology,* 1993, 67, 2142–2148), the encephalomyocarditis virus (EMCV; R. J. Kaufman e al. , *Nucleic Acids Research,* 1991, 19, 4485–4490), the foot-and-mouth disease virus (FMDV; N. Luz and E. Beck, *J. Virology,* 1991, 6486–6494), or alternatively from another origin. The content of these three articles is incorporated by reference. The cassette for expression of two genes would therefore have the following minimum structure: promoter—gene 1—IRES—gene 2—polyadenylation signal. The recombinant live vaccine according to the invention may therefore comprise, inserted into the insertion locus, an expression cassette comprising in succession a promoter, two or more genes separated in pairs by an IRES, and a polyadenylation signal.

In addition to the insertion into the locus according to the invention, it is possible to carry out one or more other insertions, one or more mutations, or one or more deletions elsewhere in the genome; if the parental strain is virulent, it is possible, for example, to inactivate (by deletion, insertion or mutation) genes involved in the virulence, such as the thymidine kinase gene, the ribonucleotide reductase gene, the gE gene and the like. In any case, the insertion into a locus other than that described in the invention makes it possible to express other genes.

The subject of the present invention is also a vaccine against ILT, comprising a recombinant ILTV virus into which there has been inserted upstream of the genes encoding major ILTV immunogens, preferably the genes coding for gB (A. M. Griffin, *J. Gen. Virol.* 1991. 72. 393–398), or for gD (M. A. Johnson et al., *DNA Sequence–The Journal of Sequencing and Mapping* 1995. Vol. S. pp 191–194. Harwood Academic Publishers GmbH), or for gp60 (K. K. Kongsuwan at al., *Virus Genes* 1993. 7. 297–303), an exogenous promoter, in particular a strong promoter as described above. This makes it possible to increase the level of expression of one or more of these genes and thus to lead to a vaccine having increased efficacy against ILT. It is of course possible to combine this with a construction as described above comprising the insertion of a heterologous sequence into the insertion locus.

The subject of the present invention is also a multivalent vaccine formula comprising, as a mixture or to be mixed, a vaccine as defined above with another vaccine, and especially another avian recombinant live vaccine as defined above, these vaccines comprising different inserted sequences, especially from different pathogens.

The subject of the present invention is also a method for preparing the vaccines according to the invention, as evident from the description.

The subject of the present invention is also a method of avian vaccination comprising the administration of a recombinant live vaccine or of a multivalent vaccine formula as defined above. Its subject is in particular such a method for the vaccination in ovo of one-day-old or older chicks and of adults. Various routes of administration of the vaccine may be used (see above) with a preference for the routes allowing mass vaccination by the mucosal route (aerosol, drinking water), the dose of vaccine being chosen preferably between $10^1$ and $10^4$ per animal.

The subject of the present invention is also an ILTV virus comprising at least one heterologous nucleotide sequence as described above, inserted into the insertion locus as defined above.

The subject of the invention is also a DNA fragment consisting of all or part of the sequence between nucleotides 1 and 3341 of SEQ ID No:5.

Figure 3:
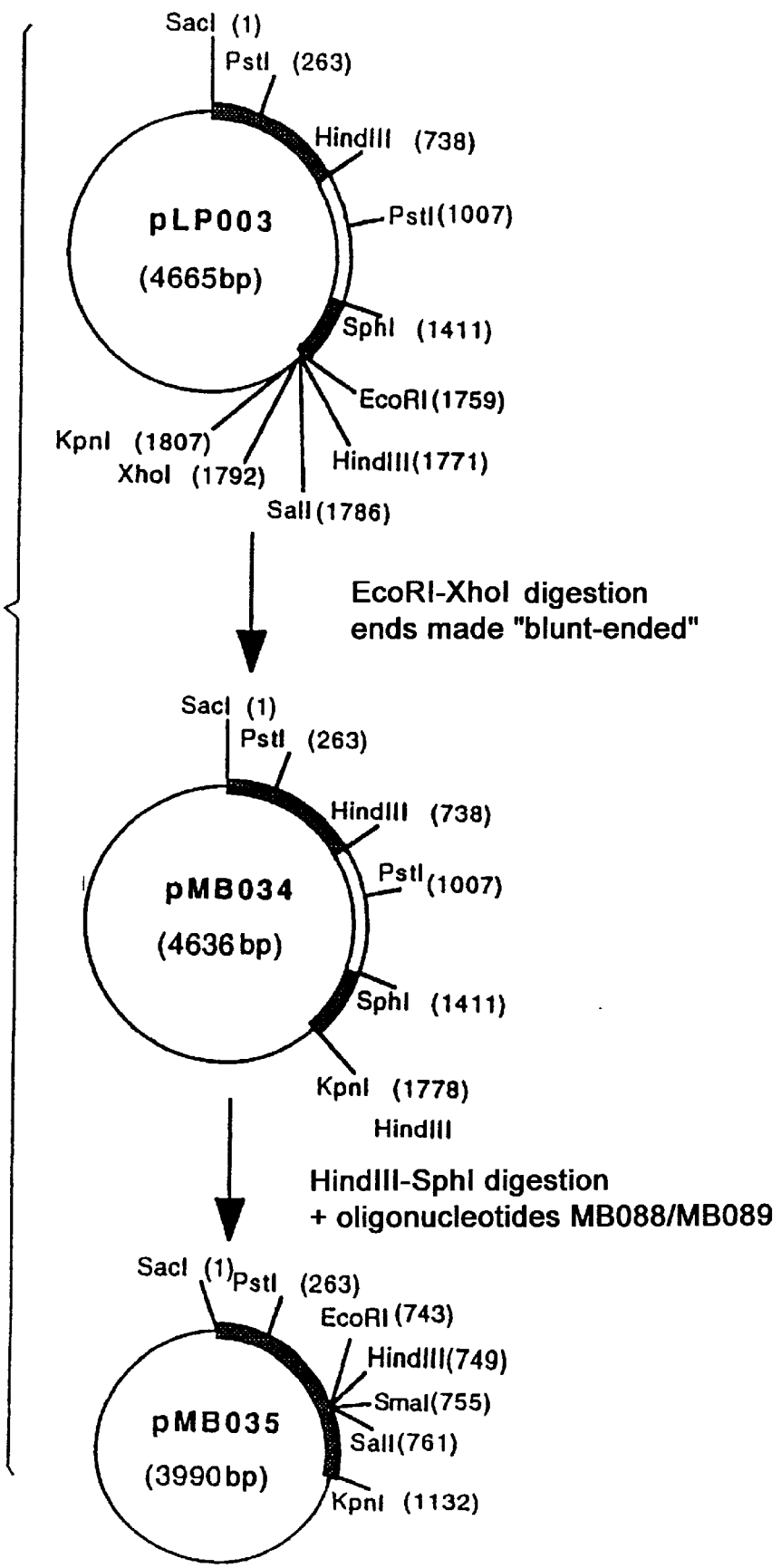
Figure 4:
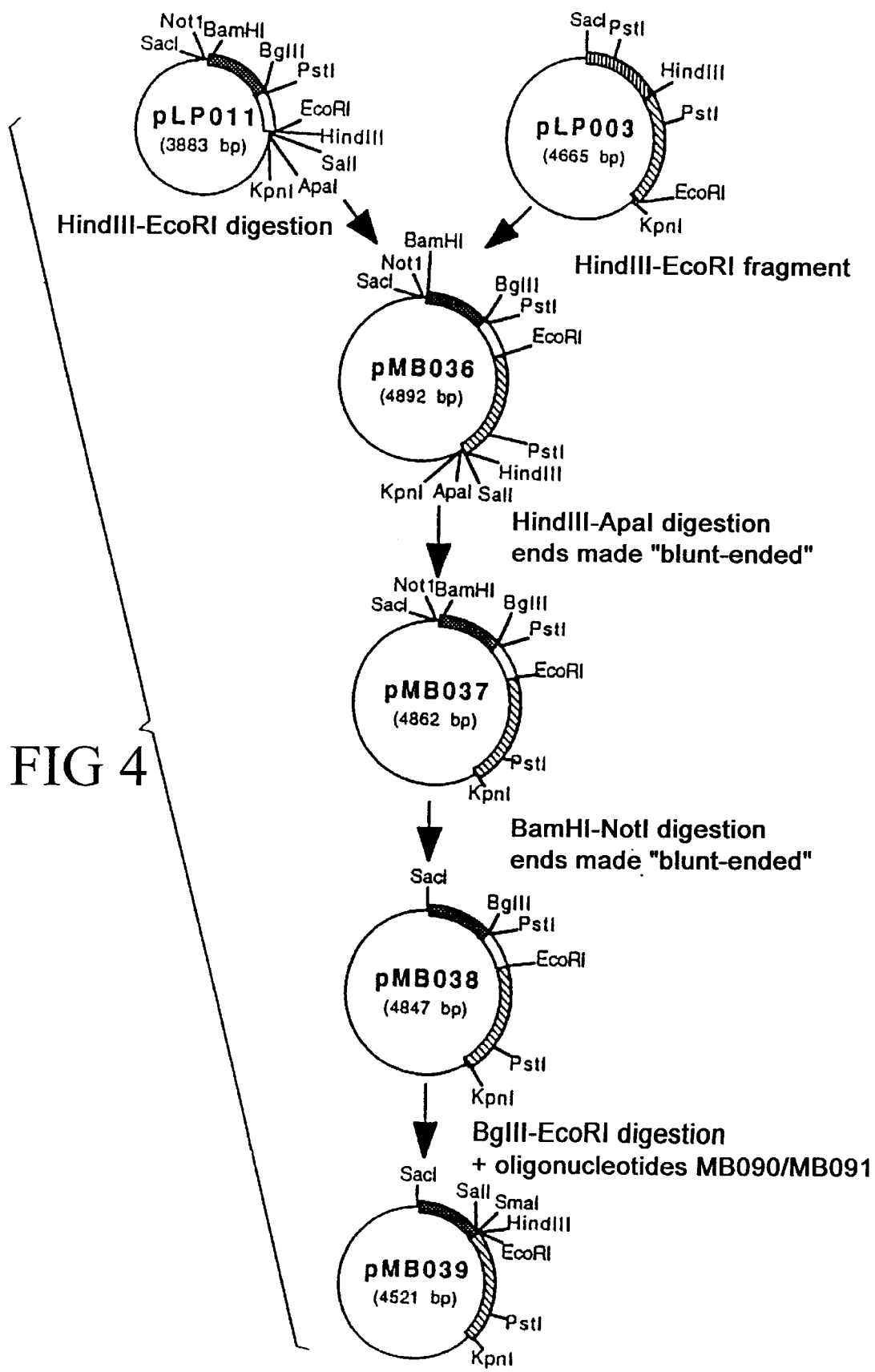
Figure 5:
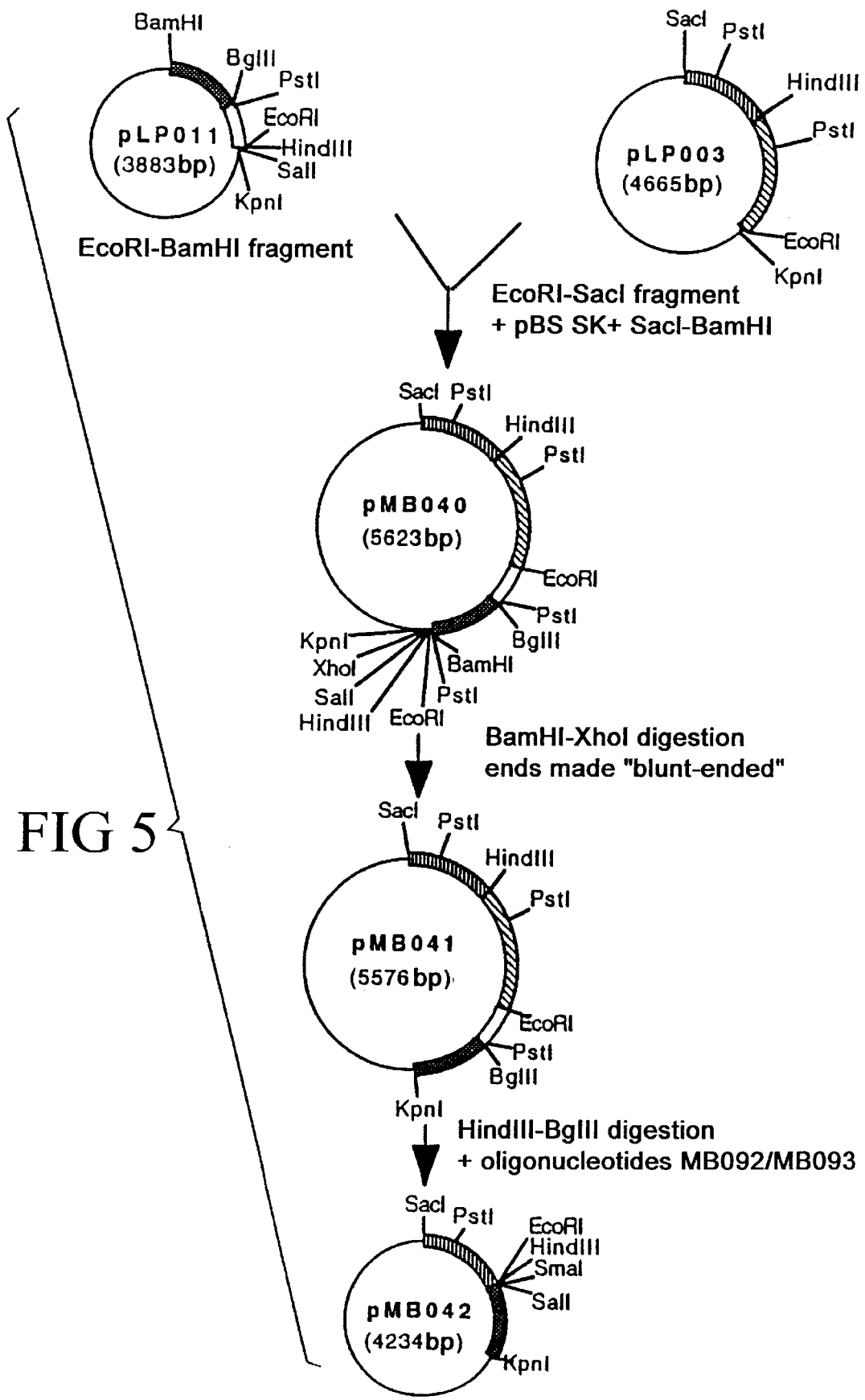
Figure 16:
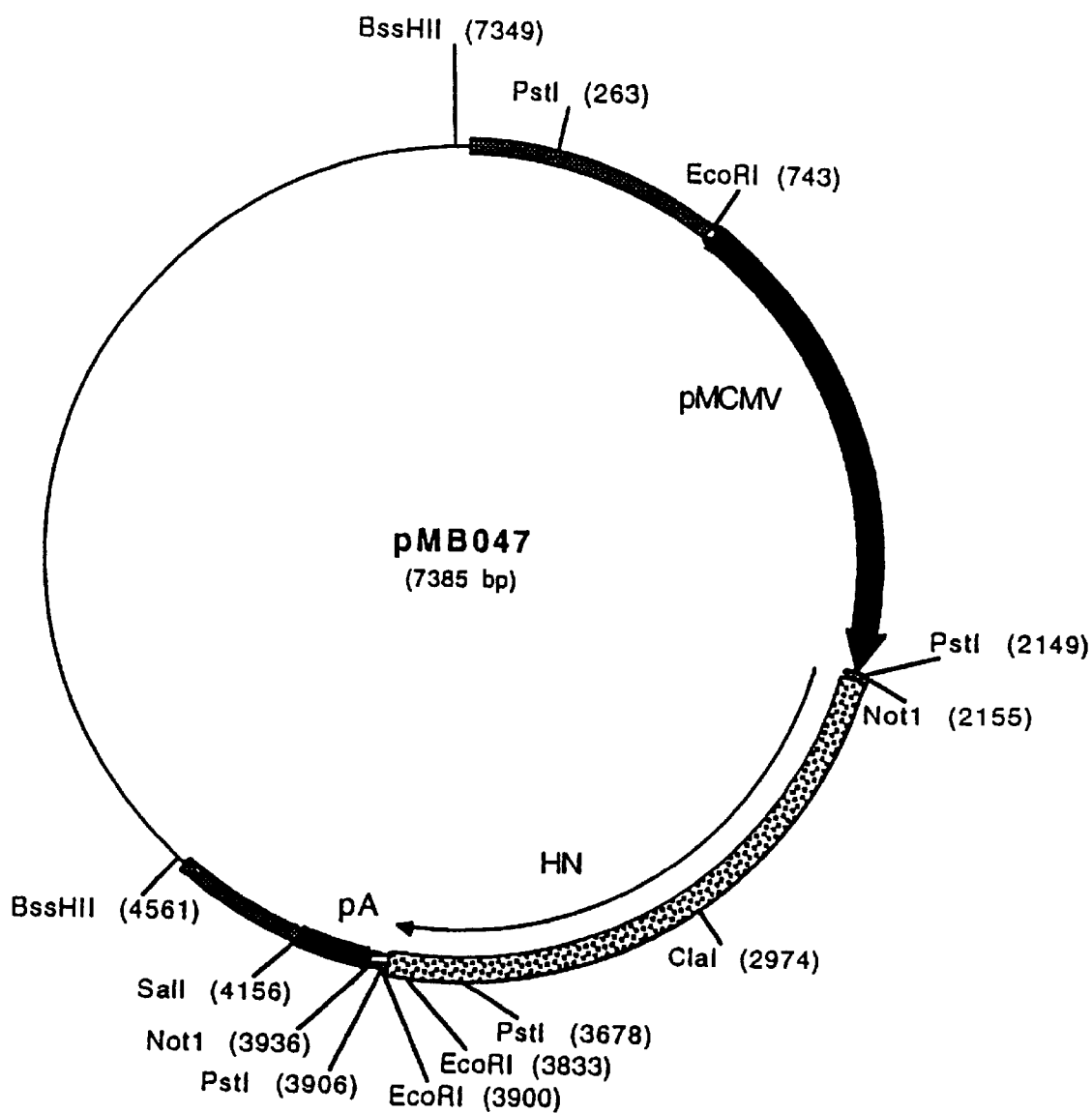

The invention will now be described in greater detail by means of the non-limiting exemplary embodiments, taken with reference to the drawing, in which:

FIG. 1: Restriction map, position of the cloned fragments and position of the ORFs FIG. 2: Sequence of 3841 bp and translation of the ORFs A, 2 and C FIG. 3: Scheme for obtaining the plasmid pMB035
FIG. 4: Scheme for obtaining the plasmid pMB039
FIG. 5: Scheme for obtaining the plasmid pMB042
FIG. 6: Scheme for obtaining the plasmid pEL024
FIG. 7: Scheme for obtaining the plasmid pEL027
FIG. 8; Diagram of the plasmid pMB043
FIG. 9: Scheme for obtaining the plasmid pCD009
FIG. 10: Scheme for obtaining the plasmid pEL070
FIG. 11: Diagram of the plasmid pMB044
FIG. 12: Diagram of the plasmid pMB045
FIG. 13; Diagram of the plasmid pMB046
FIG. 14: Sequence of the NDV HN gene
FIG. 15: Scheme for obtaining the plasmid pEL030
FIG. 16: Diagram of the plasmid pMB047
FIG. 17: Diagram of the plasmid pEL033
FIG. 18: Diagram of the plasmid pMB048
FIG. 19: Diagram of the double expression cassette
FIG. 20: Diagram of the plasmid pCD011
FIG. 21: Diagram of the plasmid-pMB.049

| Sequence listing: | |
|---|---|
| SEQ ID NO: 1 | Oligonucleotide EL207 |
| SEQ ID NO: 2 | Oligonucleotide EL208 |
| SEQ ID NO: 3 | Oligonucleotide LP018 |
| SEQ ID NO: 4 | Oligonucleotide LP020 |
| SEQ ID NO: 5 | Sequence of the sequenced SalI-BamHI fragment (3841 bp; see FIG. 2) |
| SEQ ID NO: 6 | Oligonucleotide MB088 |
| SEQ ID NO: 7 | Oligonucleotide MB089 |
| SEQ ID NO: 8 | Oligonucleotide MB090 |
| SEQ ID NO: 9 | Oligonucleotide MB091 |
| SEQ ID NO: 10 | Oligonucleotide MB092 |
| SEQ ID NO: 11 | Oligonucleotide MB093 |
| SEQ ID NO: 12 | Oligonucleotide MB070 |
| SEQ ID NO: 13 | Oligonucleotide MB071 |
| SEQ ID NO: 14 | Sequence of the NDV HN gene (see FIG. 14) |
| SEQ ID NO: 15 | Oligonucleotide EL071 |

| -continued | |
|---|---|
| Sequence listing: | |
| SEQ ID NO: 16 | Oligonucleotide EL073 |
| SEQ ID NO: 17 | Oligonucleotide EL074 |
| SEQ ID NO: 18 | Oligonucleotide EL075 |
| SEQ ID NO: 19 | Oligonucleotide EL076 |
| SEQ ID NO: 20 | Oligonucleotide EL077 |
| SEQ ID NO: 21 | Oligonucleotide CD001 |
| SEQ ID NO: 22 | Oligonucleotide CD002 |
| SEQ ID NO: 23 | Oligonucleotide CD003 |
| SEQ ID NO: 24 | Oligonucleotide CD004 |

EXAMPLES

All the constructions of plasmids were carried out using the standard molecular biology techniques described by Sambrook J. et al. (*Molecular Cloning: A Laboratory Manual* 2nd Edition. Cold Spring Harbor Laboratory, Cold Spring Harbor, New York. 1989). All the restriction fragments used for the present invention were isolated using the "Geneclean" kit (BIO101 Inc. La Jolla, Calif.).

The virus used as parent virus may be chosen from the vaccinal strains described in J. R. Andreasen et al. (*Avian Diseases* 1990. 34. 64–656) or the strain T-20 12 8-66 obtained from Select laboratories 10026 Main Street P.O. Box 6 Berlin, Md. 21811, USA. It is also possible to use virulent strains such as the strain N-71851 (ATCC VR-783) or the strain 83-2 from USDA, which may he attenuated by known techniques, for example that described in WO-A-95/08622.

Example 1

Culture of the ILTV Virus

The ILTV virus is cultured on primary chicken kidney cells (CKC); these cells are cultured in MEM medium supplemented with 3 k foetal calf serum (FCS) in 75 cm. culture flasks ($2 \times 10^5$ cells/cm²) one or two (says before inoculation.

On the day of inoculation, a flask of 1000 doses of freeze-dried vaccine is resuspended in 10 ml of MEM medium supplemented with 1% FCS; about 0.5 ml of this solution is then deposited on the CKC culture. On the next day, the medium is changed, and the day after, is when the cytopathogenic effect (CPE) becomes generalized, the culture flasks are frozen at −70° C.

The culture of the ILTV virus can also be carried out on immortalized chicken liver cells, and in particular on the LMH line (W. M. Schnitzlein et al., *Avian Diseases* 1994. 38. 211–217).

Example 2

Preparation of the ILTV Genomic DNA

After 2 freeze/thaw cycles, the ILTV culture (2 flasks of 75 cm²) is harvested and centrifuged at low speed (5000 rpm in a 20 rotor, Beckman JA21 centrifuge, for 5 minutes) to remove the large cell debris. The supernatant is then ultra-centrifuged (100,000 rpm, TLA100.3 rotor, Beckman TL100 centrifuge, for 1 hour).

The pellet is then taken up in 1.6 ml of TEN-SDS (10 mM Tris pH 8.0; 1 mM EDTA; 0.5 M NaCl; 0.5% sodium dodecyl sulphate), and 35 μl of a proteinase K solution at 20 mg/ml are then added; the solution is incubated for 3 to 4 hours on a water bath at 37° C., and the DNA is then extracted 3 times with phenol/chloroform and once with chloroform, then it is precipitated with ethanol at −20° C. After centrifugation, the pellet is rinsed with 70% ethanol, dried and resuspended in 200 μl of TE (10 mM Tris pH 8.0; 1 mM EDTA). The nucleic acid concentration is then assayed in a spectrophotometer ($OD_{260}$). This DNA solution can serve directly as template for the polymerase chain reaction (PCR) experiments; likewise, it can also be used in the transfection experiments for obtaining a recombinant virus.

Example 3

Isolation and purification of the Recombinant ILTV Virus

The donor plasmid composed of a cassette for expressing a polypeptide inserted between two flanking regions of the insertion locus is digested with a restriction enzyme allowing the linearization of the plasmid, then it is extracted with a phenol/chloroform mixture, precipitated with absolute ethanol, and taken up in sterile water. 24-Hour primary CKC cells are then transfected with the following mixture: 0.2 to 1 μg of linearized donor plasmid +2 to 5 μg of ILTV viral DNA (prepared as in Example 2) in 300 μl of OptiMEM (Gibco BRL Cat# 041–01985H) and 100 μg of LipofectAMINE diluted in 300 μl of medium (final volume of the mixture=600 μl). These 600 μl are then diluted in 3 ml (final volume) of medium and plated on 5×10 CKC. The mixture is left in contact with the cells for 5 hours, then removed and replaced with 5 ml of culture medium. The cells are then left in culture for 3 to 8 days at +37° C., then, when the cytopathogenic effect has appeared, they are frozen at −70° C. After thawing and optionally sonicating, this viral population is cloned at limiting dilution in microplates (96 well) in order to isolate a homogeneous recombinant virus population. These plates are left in culture for 1 to 3 days, then the supernatant is harvested in an empty 96-well plate and the plate containing the supernatants is placed at 4° C. or at −70° C. The cells remaining in the other plates are then fixed with 95% acetone for 20 to 30 minutes at −20° C., or for 5 minutes at room temperature. An indirect immunofluorescence (IIF) reaction is carried out with a monoclonal antibody directed against the polypeptide expressed in order to seek out the plaques expressing this polypeptide. Another cloning is then carried out in the same manner (at limiting dilution in 96-well plates) from the supernatant present in the wells of the slates placed at 40° C. or at −70° C. and corresponding to the wells having positive plaques in IIF. In general, 4 successive isolation cycles (limiting dilution, harvesting of the supernatant, monitoring of the cells by IIF, limiting dilution from the supernatant and the like) are sufficient to obtain recombinant viruses whose entire progeny exhibits a specific fluorescence. The genomic DNA of these recombinant viruses is characterized at the molecular level by conventional PCR and Southern blotting techniques using the appropriate oligonucleotides and DNA probes.

The isolation of the recombinant virus may also be carried out by hybridization with a probe specific for the inserted expression cassette. For that, the viral population harvested after transfection is diluted and deposited on CKC cells (cultured in a Petri dish) so as to obtain isolated plaques. After 1 hour of contact at 37° C., the infection medium is removed and replaced with 5 ml of MEM medium containing 1% agarose, maintained superfused at 42° C. When the agarose has solidified, the dishes are incubated for 48 to 72 hours at 37° C. in a $CO_2$ incubator until plaques appear. The agarose layer is then removed and the viral plaques are transferred onto a sterile nitrocellulose membrane having the same diameter as the Petri dish which served for the culture. This membrane is itself transferred onto another nitrocellulose membrane so as to obtain a reverse “copy” of the first transfer. The plaques transferred onto this latter copy are then hybridized, according to the customary techniques known to persons skilled in the art, with a digoxigenin-labelled DNA fragment of the expression cassette (DNA Labelling Kit, Boehringer Mannheim, CAT # 1175033). After hybridization, washes and contacting with the revealing substrate, the nitrocellulose membrane is placed in contact with an autoradiographic film. The images of positive hybridization on this membrane indicate the plaques which contain the recombinant ILTV viruses which have inserted the expression cassette. The plaques corresponding to these positive plaques are sterilely cut out from the first nitrocellulose membrane, placed in an Eppendorf tube containing 0.5 ml of MEM medium and sonicated to release the virions from the membrane. The medium contained in the Eppendorf tube is then diluted in MEM medium and the dilutions thus obtained serve to infect new cultures of CKC cells.

Example 4

Amplification of an ILTV Genomic Region

The oligonucleotides EL207 (SEQ ID NO:1) and EL208 (SEQ ID NO:2) served as primers for a first amplification by the polymerase chain reaction (PCR).

EL207 (SEQ ID NO:1): 5'AAGTATACTCGAAACTAGCGCAGTACTCTG 3'

EL2S08 (SEQ ID NO:2): 5'AGATGCGATACCATTTTTACTGCCArrTGG 3'

The first PCR was carried out in the presence of the oligonucleotides EL207 and EL208, of PCR buffer, DNTP, ILTV DNA, Taq polymerase and an anti-Taq antibody (TaqStart Antibody, Clontech Lab., Palo Alto, Calif., USA) in order to limit the non-specific amplifications. 35 cycles were performed (30 seconds at 94° C., 30 seconds at 60° C. and 8 minutes at 72° C.). The placing of an aliquot of the reaction product on an electrophoresis gel made it possible to detect an amplified DNA band of about 7 kb.

A second PCR, carried out with the oligonucleotides LP018 (SEQ ID NO:3) (position from 2677 to 2696 on the sequence SEQ ID NO:S) and LP020 (SEQ ID NO:4), made it possible to amplify a fragment of 1190 bp.

LP018 (SEQ ID NO:3): 5'TCGTGTCTCTGCTATCACTG 3'

LP020 (SEQ ID NO:4): 5'AGCTCTCCATGGATCTAGCG 3'

Example 5

Cloning add characterization of this ILTV Genomic Region

The product of the first gene amplification reaction was purified by phenol/chloroform extraction and then digested with the restriction enzymes EcoRI and Sacd for 2 hours at 37° C. The restriction enzymes were then inactivated by heating the tubes at 65° C. for 20 minutes. The fragments resulting from this digestion were then ligated (overnight at 14° C.) with the plasmid pBlueScriptII SK+(pBS SK+; Stratagene) digested with EcoRI and SacI; the analysis of the clones obtained after transformation of *E. coli* DH5α. bacteria and culture on dishes of ampicilin-supplemented medium made it possible to identify 3 EcoRI-SacI inserts of different size present in 3 different plasmids: a fragment of about 0.5 kb (plasmid pLP001), of 2.8 kb (plasmid pLP002) and of 1.8 kb (plasmid pLP003).

The amplification product of the second PCR reaction was purified as above, digested with the enzymes EcoRI and BamHI and cloned into the plasmid pBS SK+previously digested with EcoRI and SamRI to obtain the clone PLP011.

Partial sequencing of the insert present in pLP002 (on the right of the SalI site, see FIG. 1) and complete sequencing of that present in pLP003 and in pLP011 made it possible to identify two complete open reading frames (ORFS) (ORF A and ORF B), and the N-terminal part of another ORF (ORF C). The restriction map of this cloned genomic region and of the sequenced region, as well as the position on this map of the inserts of the clones pLP001, pLP002,.pLP003 and pLP011 are shown in FIG. 1; the 3841 bp sequence (SEQ ID NO:5) is shown in FIG. 2. The position and the amino acid sequence of the ORFs A, B and C are also shown in FIGS. 1 and 2 respectively.

The sequence between the STOP codon of the ORF A (position 1624 on SEQ ID NO:S) and the ATG codon of the ORF C (position 3606 on SEQ ID NO:5), comprising especially the ORF B, followed by the intergenic region between the ORFs 3 and C can be used to insert cassettes for expressing polypeptides into the ILTV genome. This sequence is called insertion locus. The insertion may be made with or without deletion in ORP B (see Example 6) or in the intergenic region (see Example 7); the deletion may also cover all or part of ORF B and all or part of the intergenic region (see Example 8).

Example 6

Construction of the donor plasmid pB035 for insertion into ORF B

The plasmid pLP003 (4665 bp) was digested with the enzymes EcoRI and XhoI; this digested plasmid was then treated with DNA polymerase (Klenow fragment) in the presence of dTP to make the ends blunt; after ligation and transformation of the *E. coli* bacteria, the clone pMB034 (4636 bp) was obtained; this cloning step made it possible to delete the cloning sites between EcoRI and XhoI in the plasmid pLP003.

The plasmid pMB034 was then digested with the enzymes HindIII and SphI; the 4.0 kbp fragment was then eluted and ligated to the oligonucleotides MS088 (SEQ ID NO:6) and MB089 (SEQ ID NO:7) previously hybridized. The plasmid pMP035 (39–90 bp) was thus obtained after transformation of *E. coli* bacteria (see scheme for obtaining pMB035 in FIG. 3).

MB088 (SEQ ID NO:6): 5'AGCTGAATTCAAGCTTC-CCGGGGTCGACATG 3'

MB89 (SEQ ID NO:7): 5'TCGACCCC GG=AAC TTC 3'

This plasmid pMB035 therefore contains: (1) a homologous sequence in 5' of ORF B, (2) an inserted oligonucleotide sequence containing the unique EcoRI, SmaI, HindIII and SalI sites, and (3) a homologous sequence in 3' of the ORF B. This plasmid therefore makes it possible to introduce an expression cassette into the unique sites mentioned in (2) placed between the 2 flanking regions (1) and (3). The recombinant ILTV viruses obtained will have a deletion in ORF B (between the HindIII and SphI sites; amino acids 56 to 279 of ORF B deleted).

Example 7

Construction of the Donor Plasmid p=39 for Insertion unto the Intergenic Region Between the ORFs B and C The plasmid pLP011 (3883 bp) was digested with the enzymes EcoRI and HindIII and ligated to the 1021 bp restriction fragment obtained by digesting the plasmid pLP003 (4665 bp) with the enzymes EcoRI and HindIII; the plasmid thus obtained (pMB036) has a size of 4892 bp. The plasmid pME036 was digested with the enzymes HindIII and ApaI; the digested plasmid was then treated with DNA polymerase (Klenow fragment) in the presence of dTP to make the ends blunt; after ligation and transformation of *E. coli* bacteria, the clone pMB037 (4862 bp) was obtained; this cloning step made it possible to delete the cloning sites between HindIII and ApaI in the plasmid pME036.

The plasmid pMB037 was digested with the enzymes NotI and BamRI; the digested plasmid was then treated with DNA polymerase (Klenow fragment) in the presence of dNTP to make the ends blunt; after ligation and transformation of *E. coli* bacteria, the clone pMB038 (bp) was obtained; this cloning step made it possible to delete the cloning sites between NotI and BamHI in the plasmid pMR037.

The plasmid pMB038 was then digested with the enzymes BglII and EcoRI; the 4.5 kbp fragment was then eluted and ligated to the oligonucleotides MB090 (SEQ ID NO:8) and MB091 (SEQ ID NO:9) previously hybridized. The plasmid pMB039 (bp) was thus obtained after transformation of *E. coli* bacteria (see scheme for obtaining pMB039 in FIG. 4).

ME090 (SEQ ID NO:8): 5'GATCGTCGACCCCGG-GAAGCTTG 3'

MB091 (SEQ ID NO:9): 5'AATTCAAGCTTC-CCGGGGTCGAC 3'

This plasmid pME039 therefore contains: (1) a homologous sequence in 5' in ORF B, (2) an inserted oligonucleotide sequence containing the unique EcoRI, SmaI, HindIII and SailI sites, and (3) a homologous sequence in 3' of the intergenic region between the ORFs B and C. This plasmid therefore makes it possible to introduce an expression cassette into the unique sites mentioned in (2) placed between the 2 flanking regions (1) and (3). The recombinant ILTV viruses obtained will have a 344 bp deletion in the intergenic region between the ORFs B and C (between the EcoRI and BglII sites).

Example 8

Construction of the Donor Plasmid pMB042 for Insertion into the Genomic Region Overlapping ORF B and the Intergenic Region Between the ORFs B and C The 940 bp fragment obtained by digesting the plasmid pLP011 (3883 bp) with the enzymes BamHI and EcoRI, and the 1754 bp fragment obtained by digesting the plasmid pLP003 (4665 bp) with the enzymes EcoRI and SacI were ligated into the plasmid pBS SK+ digested with the enzymes BamHI and SacI; the plasmid thus obtained (pMB040) has a size of 5623 bp The plasmid pMB039 was digested with the enzymes BamHI and XhoI; the digested plasmid was then treated with DNA polymerase (Kienow fragment) in the presence of dNTP to make the ends blunt; after ligation and transformation of *E. coli* bacteria, the clone pMB041 (5576 bp) was obtained; this cloning step made it possible to delete the cloning sites between BamHI and XhoI in the plasmid pMB040.

The plasmid pMB041 was then digested with the enzymes HindIII and BglII; the 4.2 kbp fragment was then eluted and ligated to the oligonucleotides MB092 (SEQ ID No: 10) and MB093 (SEQ ID NC:11) previously hybridized. The plasmid pMB042 (4234 bp) was thus obtained after transformation of *E. coli* bacteria (see scheme for obtaining pMB042 in FIG. 5).

MB092 (SEQ ID NO:10): 5'AGCTGAATTCAACCTTC-CCGGGGTCGAC 3'
MS093 (SEQ ID NO:11): 5'GATCGTCGACCCCGG-GAAGCTTGAATTC 3'

This plasmid pMB042 therefore contains: (1) a homologous sequence in 5' of ORF B, (2) an inserted oligonucleotide sequence containing the unique EcoRI, SmaI, HindIII and SalI sites, and (3) a homologous sequence in 3' of the intergenic region between the ORFs B and C. This plasmid therefore makes it possible to introduce an expression cassette into the unique sites mentioned in (2) placed between the 2 flanking regions (1) and (3). The recombinant ILTV viruses obtained will have a 1366 bp deletion covering the C-terminal part of ORF B (the 339 c-terminal amino acids of ORF B) and the 5' part of the intergenic region between the ORFs B and C (between the HindIII and BglII sites, noted on FIG. 1).

Example 9

Construction of the Donor Plasmid pMB043 for the Insertion of a Cassette for Expressing the IBDV VP2 Gene Under the Control of the HCMV IE Promoter into the ORE B site isolation of vILTV 1

Figure 6:
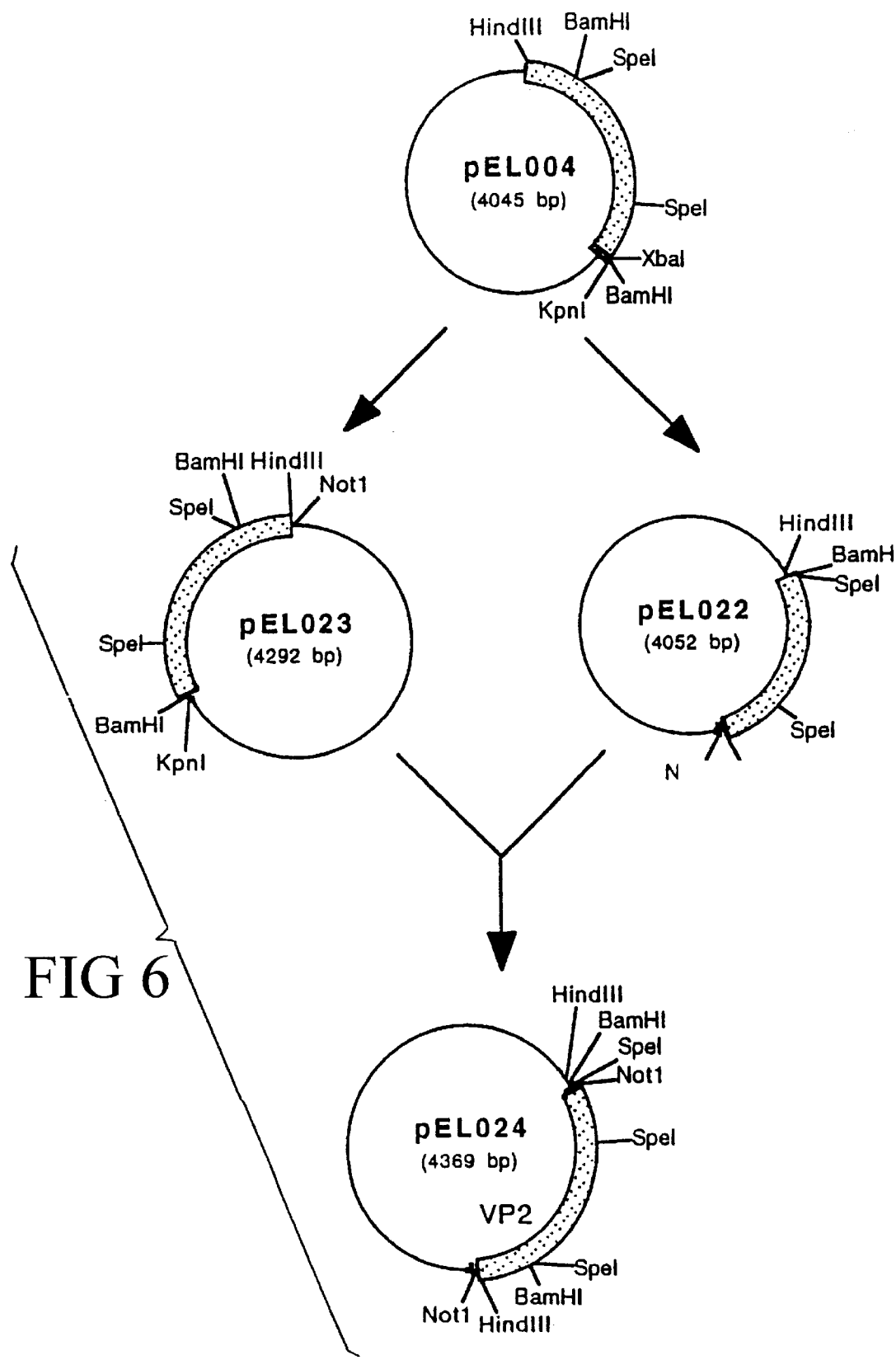

9.1—Cloning of the VP2 gene from the infectious bursal disease virus (IBDV) and construction of a cassette for expressing VP2 under the control of the HCMV IE promoter The plasmid pEL004 (see FIG. 6;=plasmid pGH004 described in French patent application 92,13109) containing the IBDV VP2 gene in the form of a BamHI-HindIII cassette was digested with BamHI and XbaI in order to isolate the BamHI-XbaI fragment (truncated VP2 gene) of 1104 bp. This fragment was cloned into the vector pBS SK+, previously digested with XbaI and BamHI to give the 4052 bp plasmid pEL022 (FIG. 6). The vector pBS-SK+was digested with EcoRV and XbaI, then self-ligated to give pBS-SK⁻ (modified). The plasmid pEL004 was digested with KpnI and HindIII in order to isolate the 1387 bp KpnI-HindIII fragment containing the complete IBDV VP2 gene. This fragment was cloned into the vector pBS-SK⁻, previously digested with KpnI and HindIII, to give the 4292 bp plasmid pEL023 (FIG. 6). The plasmid pEL022 was digested with BamHI and NotI in order to isolate the 1122 bp BamHI-NotI fragment (fragment A). The plasmid pBL023 was digested with BamHI and NotI in order to isolate the 333 bp BamHI-NotI fragment (fragment B). The fragments A and 3 were ligated together with the vector pPS-SK+, previously digested with NotI and treated with alkaline phosphatase, to give the 4369 bp plasmid pEL024 (FIG. 6.

Figure 7:
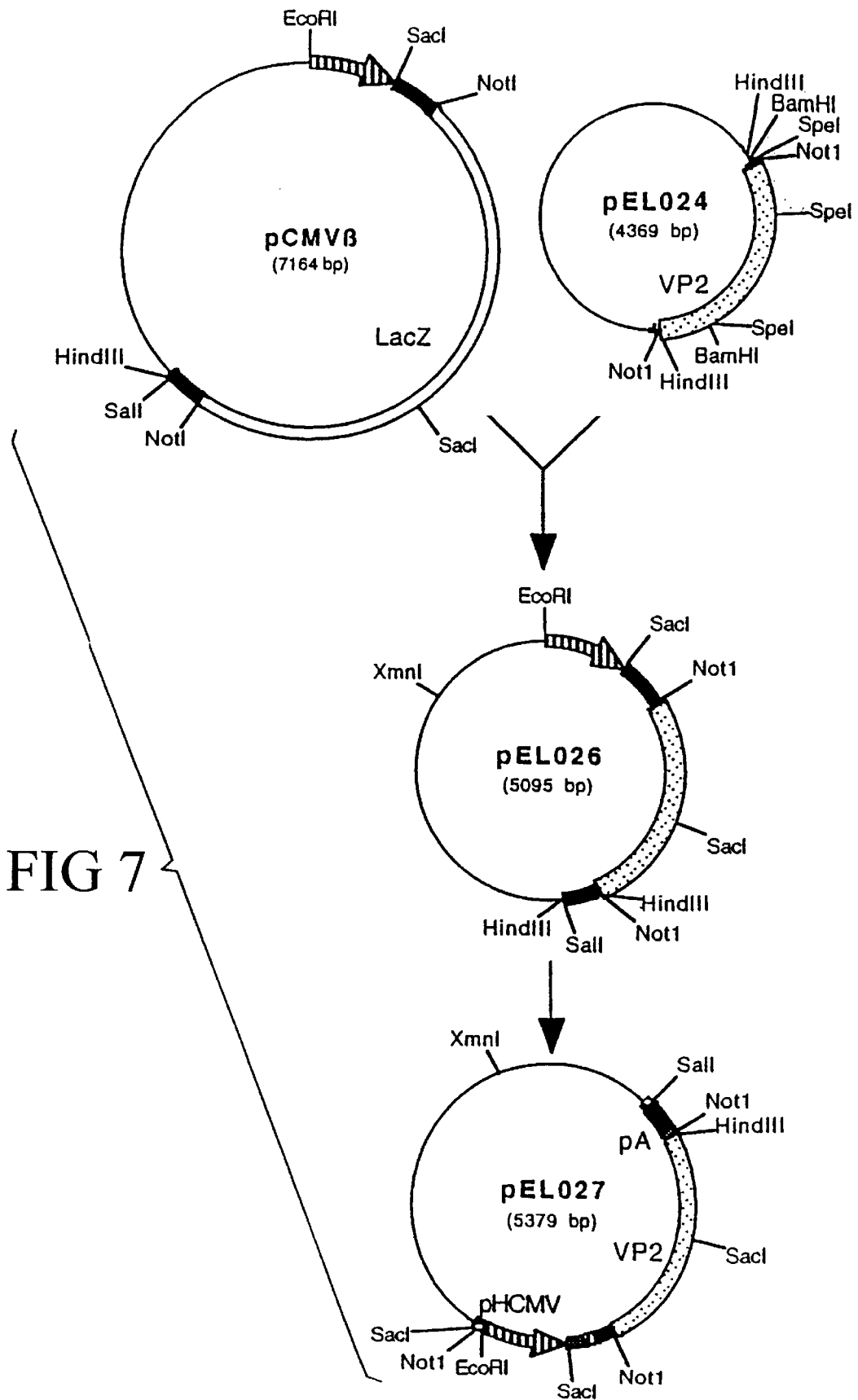

The plasmid pEL024 was digested with NotI in order to isolate the 1445 bp NotI-NotI fragment This fragment was ligated with the plasmid pCMVβ (Clontech Cat# 6177–1, FIG. 7), previously digested with NotI, to give the 5095 bp plasmid pEL026 (FIG. 7), The plasmid pEL026 was digested with EcoRI, Sal and XmnI in order to isolate the 2428 bp EcoRI-Sal fragment. This fragment was ligated with the vector pBP-SX+, previously digested with EcoRI and SalI, to give the 5379 bp plasmid pEL027 (FIG. 7).

9.2—Construction of the donor plasmid pME043

Figure 8:
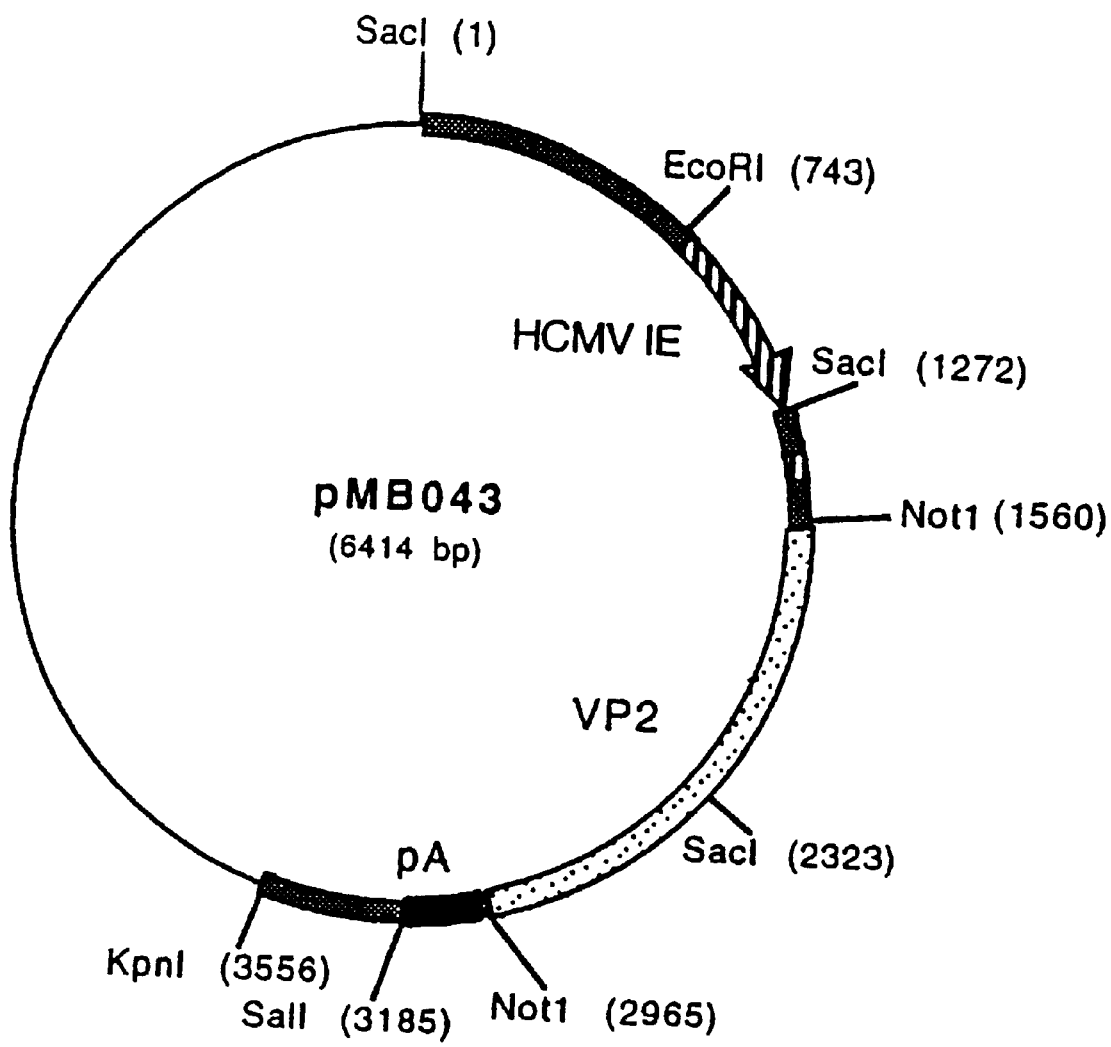

The plasmid pEL027 was digested with EcoRI, SalI and XmnI in order to isolate the 2428 bp EcoRI-SalI fragment. This fragment was ligated into the plasmid pMB035 (see Example 6 and FIG. 3), previously digested with EcoRI and SalI, to give the 6414 bp plasmid pMB043 (FIG. 8).

9.3—Isolation and purification of the recombinant vILTV1 virus

The vILTV1 virus was isolated and purified after cotransfection of the DNA from the plasmid pMB036 previously linearized with the enzyme KpnI, and of the viral DNA, as described in Example 3. This recombinant contains a cassette HCMV-IE/IBDV VP2 in the ORF B of the ILTV virus partially deleted (see Examples 5 and 6).

Example 10

Construction of the Donor Plasmid pMB044 for the Insertion of a Cassette for Expressing the IBDV the ORF B Site and Isolation of vILTV2

Figure 9:
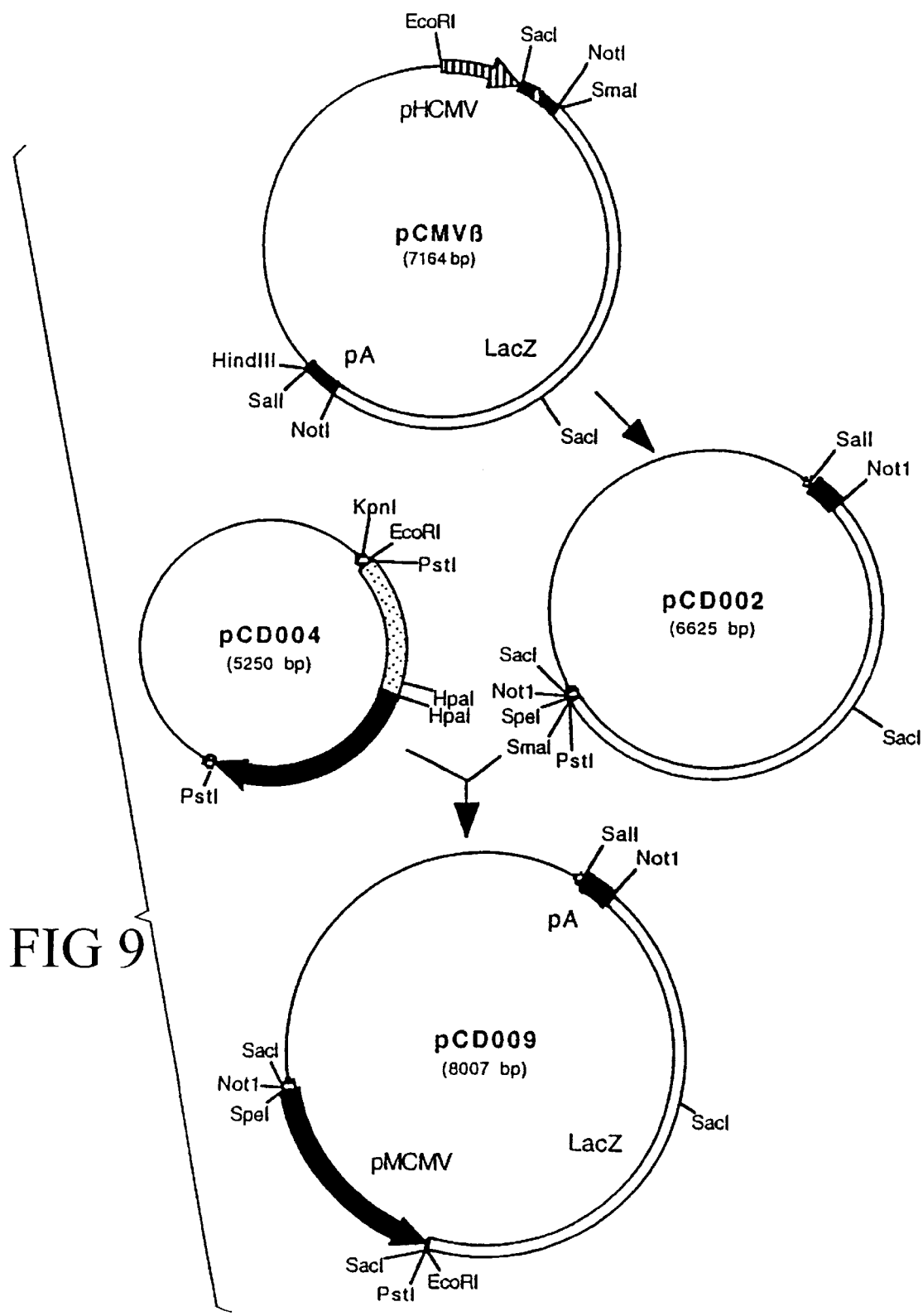

10.1 Construction of pEL070 containing a cassette for expressing the IBDV VP2 gene under the control of the mC (Mouse CytomegaloVirus) immediate early TIE) promoter The plasmid PCMVβ (Clontech Cat# 6177-1, FIG. 9) was digested with SalI and SmaI in order to isolate the 3879 bp SalI-SmaI fragment containing the lacZ gene as well as the polyadenylation signal of the SV40 virus late gene. This fragment was inserted into the vector pBS-SK+, previously digested with SalI and EcoRV, to give the 6625 bp plasmid pCD002 (FIG. 9). This plasmid contains the lacZ reporter gene but no promoter is situated upstream of this gene.

The MCMV virus, Smith strain was obtained from the American Type Culture Collection, Rockville, Md., USA (ATCC No. VR-194). This virus was cultured on Balb/C mouse embryo cells and the viral DNA from this virus was prepared as described by Ebeling A. et al. (J. Virol. 1983. 47. 421–433). This viral genomic DNA was digested with-PstI in order to isolate the 2285 bp PstI-PstI fragment. This fragment was cloned into the vector pBS-SK+, previously digested with PstI and treated with alkaline phosphatase, to give the plasmid pCD004 (FIG. 9). The plasmid pCD004 was digested with HpaI and PstI in order to isolate the 1389 bp HpaI-PstI fragment which contains the promoter/activating region of the murine cytomegalovirus Immediate-Early gene (Murine CytoMegaioVirus=MCMV) (Dorsch-Häsler K. et al. Proc. Natl. Acad. Sci. 1985. 82. 8325–8329, and patent application WO-A-87/03905). This fragment was cloned into the plasmid pCD002, previously digested with PstI and SmaI, to give the 8007 bp plasmid pCD009 (FIG. 9).

A double-stranded oligonucleotide was obtained by hybridization of the following two oligonucleotides:
MB070 (SEQ ID NO:12)
5'CGAATTCACTAGTGTGTGTCTGCAGGCG-GCCGCGTGTGTGTCGACGGTAC 3'
MB071 (SEQ ID NO:12)
5'CGTCGACACACACGCGGCCGCCTGCAGA-CACACACTAGTGAATTCGAGCT 3'

Figure 10:
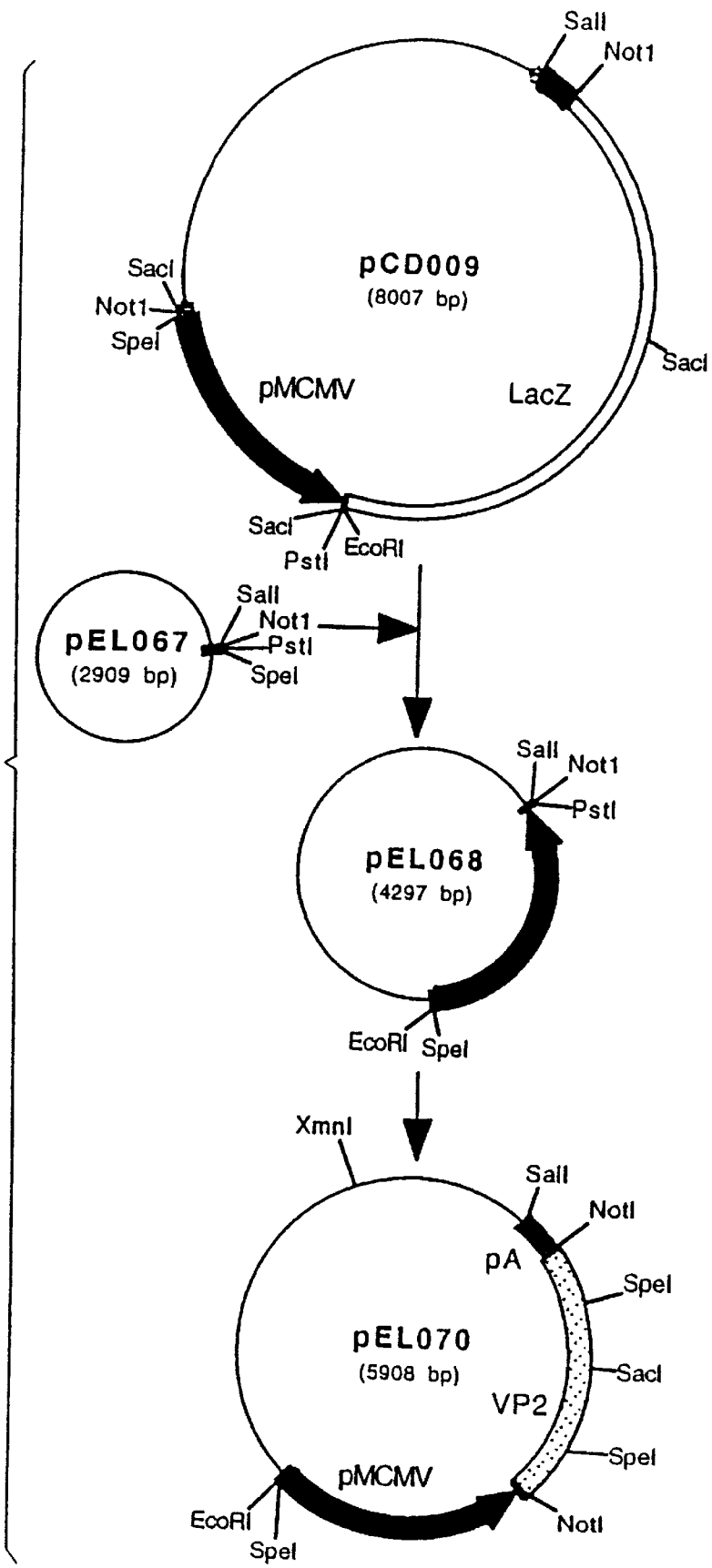

This double-stranded oligonucleotide was ligated with the vector pBS-SK+, previously digested with KpnI and SacI, to give the plasmid pEL067 (FIG. 10). The plasmid pCD009 was digested with PstI and SpeI in order to isolate the 1396 bp PstI-SpeI fragment. This fragment was ligated with the plasmid pEL067, previously digested with PstI and SpeI, to give the 4297 bp plasmid pEL068 (FIG. 10 ). The plasmid pEL024 (see Example 9, paragraph 9.1 and FIG. 6) was digested with HindIII and NotI in order to isolate the 1390 bp HindIII-NotI fragment (fragment A). The plasmid pEL027 (see Example 9, paragraph 9.1 and FIG. 7) was digested with HindIII and SalI in order to isolate the 235 bp HindIII-SalI fragment (fragment s). The fragments A and 2 were ligated together with the plasmid pEL068, previously digested with NotI and SalI, in order to give the 5908 bp plasmid pEL070 (FIG. 10). This plasmid therefore contains an expression cassette consisting of the MCMV IE promoter, the VP2 gene and the SV40 polyA signal.

10.2—Construction of the donor plasmid pMB044

Figure 11:
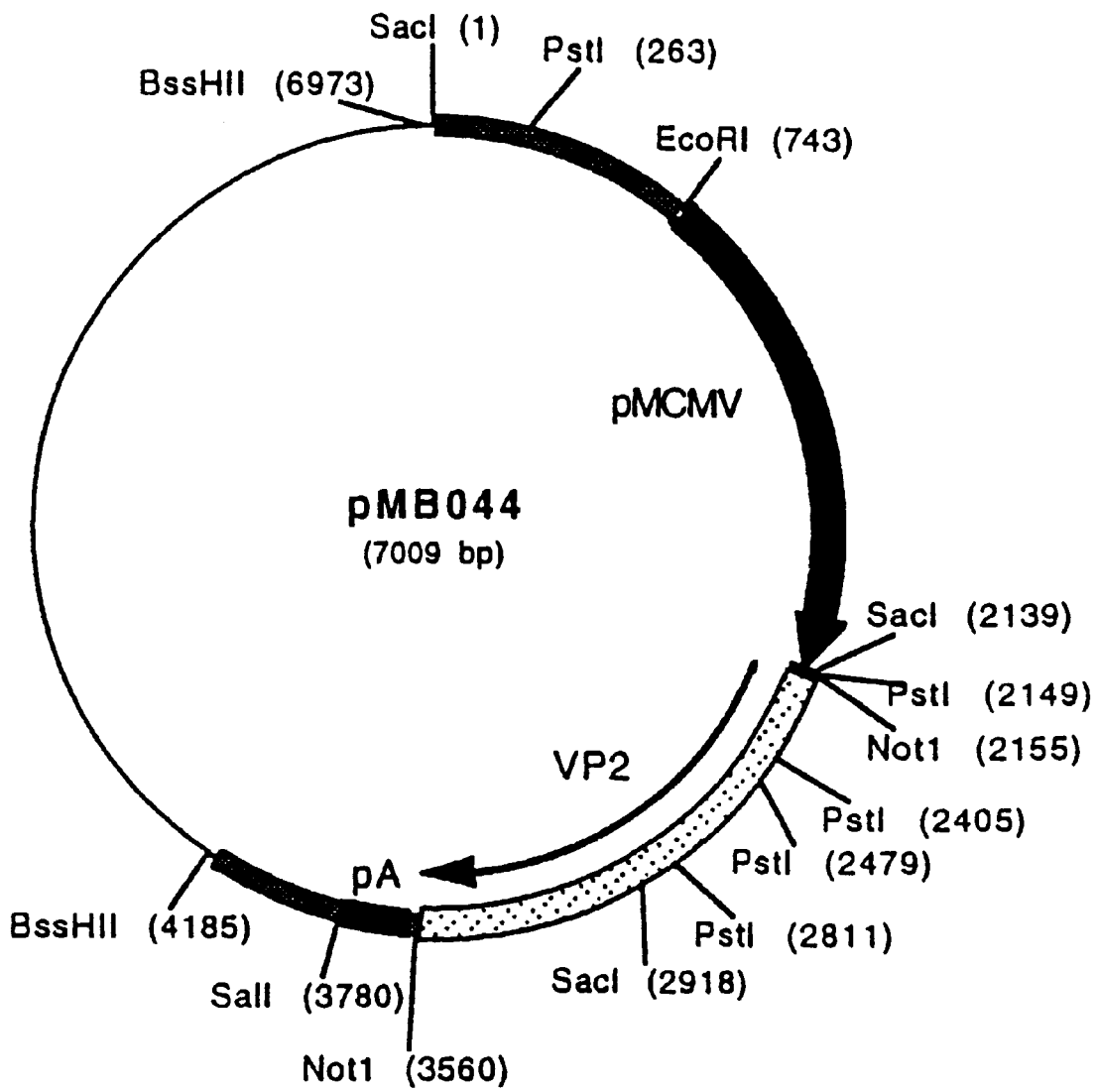
Figure 12:
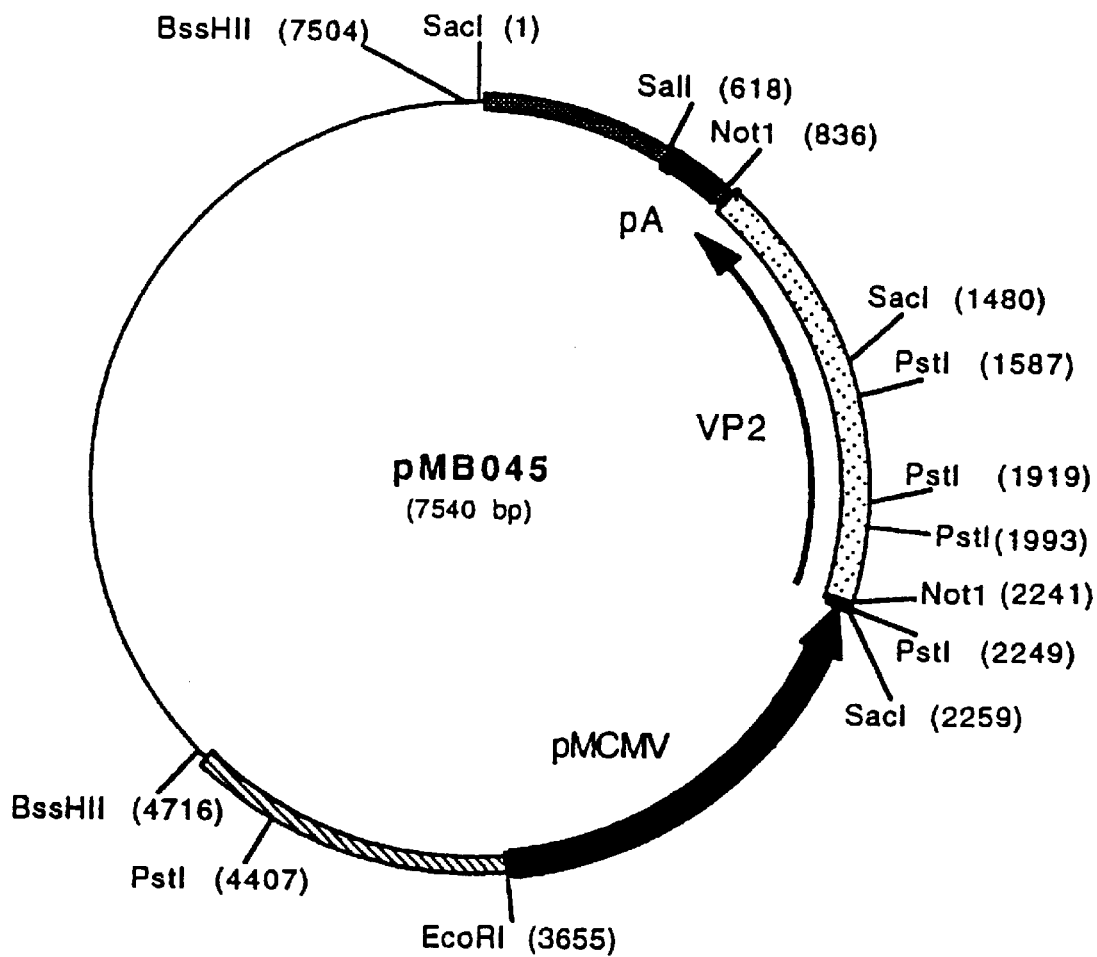

The plasmid pEL070 was digested with EcoRI, SalI and XmnI in order to isolate the 303S bp EcoRI-SalI fragment. This fragment was ligated into the plasmid pMB035 (see Example 6 and FIG. 3), previously digested with EcoRI and SalI, in order to give the 7009 bp plasmid pMB044 (FIG. 11). This plasmid allows the insertion of the expression cassette MCMV-IE/IBDV-VP2 into the partially deleted ORF B of the ILTV virus.

10.3—Isolation and purification of the -vILTV2 recombinant virus

The vILTV2 virus was isolated and purified after cotransfection of the DNA from the plasmid pMB044 previously linearized with the enzyme BssHII and of the viral DNA, as described in Example 3. This recombinant contains a cassette MCMV-IE/IBDV VP2 in the partially deleted ORF B of the ILTV virus (see Examples 5 and 6).

Example 11

Construction of the Donor plasmid -PB45 for the Insertion of a Cassette for Expressing the IBDV VP2 Gene Under the Control of the MCMV IE Promoter into the Intergenic Site Between the ORFs B and C. and Isolation of vILTV3

The plasmid pEL070 (see Example 10 and FIG. 10) was digested with EcoRI, SalI and XmnI in order to isolate the 3035 bp EcoRI-SalI fragment. This fragment was ligated into the plasmid pMB039 (see Example 7 and FIG. 4), previously digested with EcoRI and SalI, to give the 7S40 bp plasmid pMB045 (FIG. 12) This plasmid allows the insertion of the expression cassette MCMV-IE/IBDV-VP2 into the partially deleted intergenic region between the ORFs B and C of the ILTV virus. The vILTV3 virus was isolated and purified after cotransfection of the DNA from the plasmid pMB045 previously linearized with the enzyme BssHII and of the viral DNA, as described in Example 3. This recombinant contains a cassette MCMV-IE/IBDV VP2 inserted into the partially deleted intergenic region between the ORFs B and C of the ILTV virus (see Examples 5 and 7).

Example 12

Construction of the Donor Plasmid pB49 for the Insertion of a Cassette for Expressing the IBDV VP2 Gene Under the Control of the M=TE Promoter into the Genomic Region Overlapping the ORF B and the Intergenic Site Between the ORFs B and C. and Isolation of the ILTV4

Figure 13:
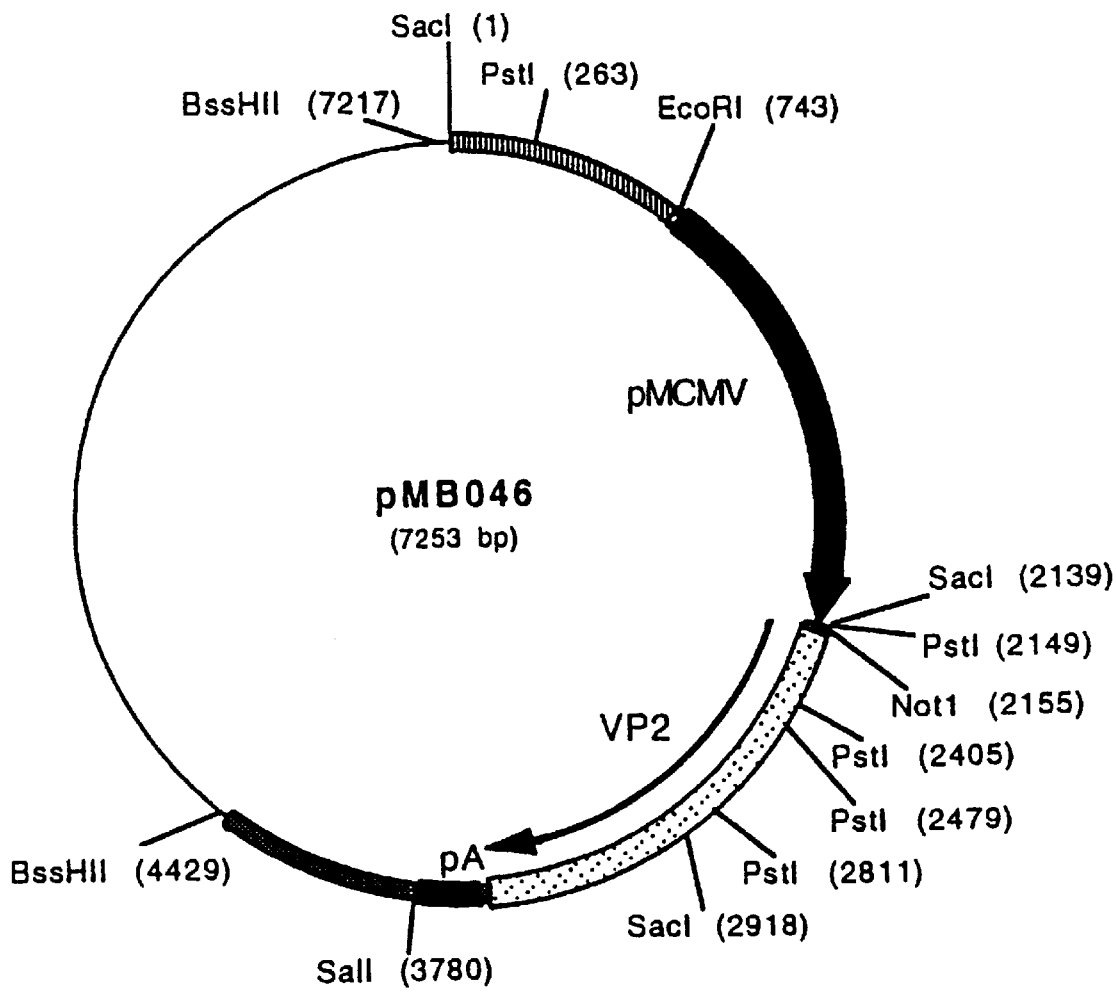

The plasmid pEL070 (see Example 10 and FIG. 10) was digested with EcoRI, SalI and XmnI in order to isolate the 3035 bp EcoRI-SalI fragment. This fragment was ligated into the plasmid pMB042 (see Example 8 and FIG. 5), previously digested with E. coli and SalI, to give the 7253 bp plasmid pMB046 (FIG. 13). This plasmid allows the insertion of the expression cassette MCMV-IE/IBDV-VP2 into the genomic region overlapping the ORF 3 and the intergenic genomic region between the ORFs B and C of the ILTV virus.

The vILTV4 virus was isolated and purified after cotransfection of the plasmid DNA pMB046 previously linearized with the enzyme BssHII and of the viral DNA, as described in Example 3. This recombinant contains a cassette MCMV-IE/IBDV VP2 inserted into the genomic region overlapping the ORF B and the intergenic genomic region between the ORFs B and C of the ILTV virus (see Examples 5 and 8).

Example 13

Construction of the Donor Plasmid 2ME047 for the Insertion of a Cassette for Expressing the NDV HN Gene into the ORF B and 4Isolation of vILTV5

13.1—Cloning of the Newcastle disease virus (NZV) HU gene

The constitution of a DNA library complementary to the genome of the Newcastle disease virus (NDV), Texas strain, was made as described by Taylor J. et al. (J. Virol. 1990. 64. 1441–1450). A clone pBR322 containing the end of the fusion gene (F), the entire haemagglutinin-neuraminidase (HN) gene and the beginning of the polymerase gene was identified as pHN01. The sequence of the NDV HN gene contained on this clone is presented in FIG. 14 (SEQ ID NO:14). The plasmid pHNOT was digested with SphI and XbaI in order to isolate the 2520 bp SphI-XbaI fragment. This fragment was ligated with the vector pUC19, previously digested with SphI and XbaI, in order to give the 5192 bp plasmid pHN02. The plasmid pHN02 was digested with ClaI and PstI in order to isolate the 700 bp ClaI-PstI fragment (fragment A). A PCR was carried out with the following oligonucleotides:

EL071 (SEQ ID NO:15) 5'CAGACCAAGCTTCT-TAAATCCC 3'

EL073 (SEQ ID NO:-16) 5'GTATTCGGGACAATGC 3' and the template pHN02 in order to produce a 270 bp PCR fragment. This fragment was digested with HindIII and PstI in order to isolate a 220 bp HindIII-PstI fragment (fragment B). The fragments A and B were ligated together with the vector pPS-SK+, previously digested with ClaI and HindIII, in order to give the 3872 bp plasmid pEL028 (FIG. 15). The plasmid pHN02 was digested with PsphI and ClaI in order to isolate the 425 bp BsphI-ClaI fragment (fragment C). A PCR was carried out with the following oligonucleotides:

EL074 (SEQ ID NO:17) 5'GTGACATCACTAGCGT-CATCC 3'EL075 (SEQ ID NO:18)

5'CCGCATCATCAGCGGCCGCGATCGGT-CATGGACGT 3' and the template pHN02 in order to produce a 465 bp PCR fragment. This fragment was digested with BsphI and NotI in order to isolate the 390 bp SsphI-NotI fragment (fragment D). The fragments C and D were ligated together with the vector pBS-SK*, previously digested with ClaI and NotI, in order to give the 3727 bp plasmid pEL029bis (FIG. 15) . The plasmid pEL028 was digested with ClaI and SacIt in order to isolate the 960 bp ClaI-SacII fragment (fragment E) . The plasmid pEL029bis was digested with ClaI and NotI in order to isolate the 820 bp ClaI-NotI fragment (fragment F). The fragments E and F were ligated together with the vector pBS-SK+, previously digested with NotI and SacII, in order to give the 4745 bp plasmid pEL030 (FIG. 15).

13.2—Construction of the plasmid pM047 containing a cassette for expressing NDV HN in the ORP B The plasmid pEL030 was digested with NotI in order to isolate the 1780 bp NotI-NotI fragment (entire NDV HN gene) . This fragment was inserted into the NotI sites of the plasmid pMB044 (Example 10, FIG. 11) in place of the 1405 bp NocI-NotI fragment containing the gene encoding the IBDV VP2 protein; this cloning made it possible to isolate the 7385 bp plasmid pMB047 (FIG. 15). This plasmid allows the insertion of the expression cassette MCMV-IE/NDV-HN into the partially deleted OPF B of the ILTV virus.

13.3—Isolation and purification of the recombinant virus vILTV5

The virus vILTV5 was isolated and purified after cotransfection of the DNA from the plasmid pMB047 previously linearized with the enzyme BssHTI and of the viral DNA, as described in Example 3. This recombinant contains a cassette MCMV-IE/NDV HN in the partially deleted ORF B of the ILTV virus (see Examples 5 and 6).

Example 14

Isolation of Other Recombinant ILTV Viruses Expressing the NDV Virus EN Gene

In a manner similar to that described in Example 13 (paragraphs 13.2 and 13.3), the HN gene flanked by NotI sites (isolated from pEL030, FIG. 15) can replace the VP2 gene in the plasmids pME045 (FIG. 12) and pMB046 (FIG. 13) in order to give plasmids allowing the isolation of recombinant viruses having a cassette for expressing the NDV D gene in the intergenic part between the ORFs B and C, or overlapping the ORF B and the intergenic part between the ORFs B and C.

Example 15

Construction of the Donor Plasmid PDM048 for the Insertion of a Cassette for Expressing the NDV F gene into the ORF B and Isolation of vILTV6

15.1—Cloning of the Newcastle disease virus (NDV) F gene

Figure 17:
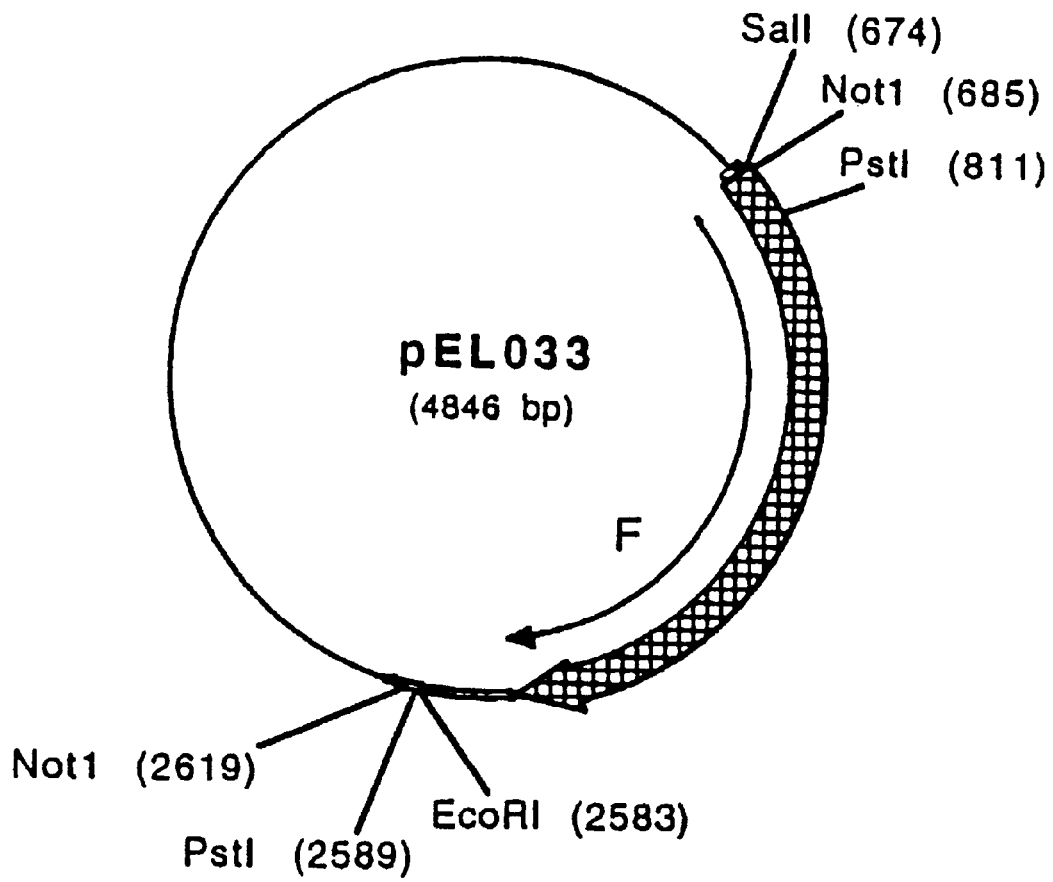

A clone derived from the DNA library complementary to the Newcastle disease virus genome (see Example 13, paragraph 13.1) and containing the entire fusion (P) gene was called pNDV81. This plasmid has been previously described and the sequence of the NDV F gene present on this close has been published (Taylor J. et al J. Virol. 1990. 64. 1441–1450). The plasmid pNDV81 was digested with NarI and PstI in order to isolate the 1870 bp NarI-PstI fragment (fragment A). A PCR was carried out with the following oligonucleotides:
EL076 (SEQ ID NO:19): TGACCCTGTCTGGATGA 3'
EL077 (SEQ ID NO:20):
5'GGATCCCGGTCCACACATTGCGCCGCAA-GATGGGC 3'
and the template pNDV81 in order to produce a 160 bp fragment. This fragment was digested with PstI and SalI in order to isolate the 130 bp PstI-SalI fragment (fragment B). The fragments A and B were ligated together with the vector pBS-SK+, previously digested with ClaI and SalI, in order to give the 4846 bp plasmid pEL033 (FIG. 17).

15.2—Construction of the plasmid pMB048 containing a cassette for expressing the NDV F gene in the ORF 2

Figure 18:
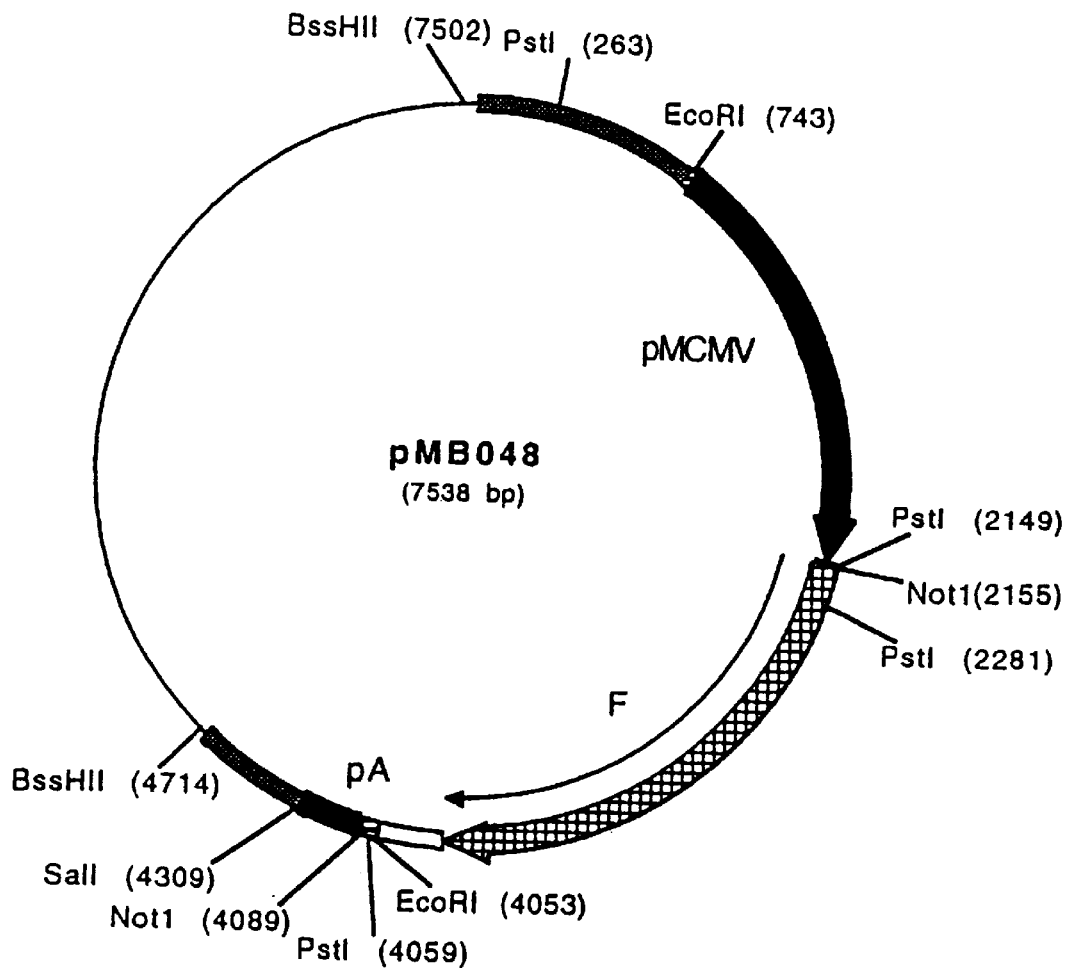

The plasmid pEL033 was digested with NotI in order to isolate the 1935 bp NotI-NotI fragment (entire F gene). This fragment was inserted into the NotI sites of the plasmid pMB044 (Example 10, FIG. 11) in place of the 1405 bp NotI-NotI fragment containing the gene encoding the IBDV VP2 protein; this cloning made it possible to isolate the 7538 .bp plasmid pMB048 (FIG. 18). This plasmid allows the insertion of the expression cassette MCMV-IE/NDV-F into the partially deleted ORF B of the ILTV virus.

15.3—Isolation and purification of the recombinant virus vILTV6

The vILTV6 virus was isolated and purified after cotransfection of the DNA from the plasmid pMB048 previously linearized with the enzyme BssHII and of the viral DNA, as described in Example 3. This recombinant contains a cassette MCMV-IE/NDV F in the partially deleted ORF B of the ILTV virus (see Examples S and 6).

Example 16

Figure 19:
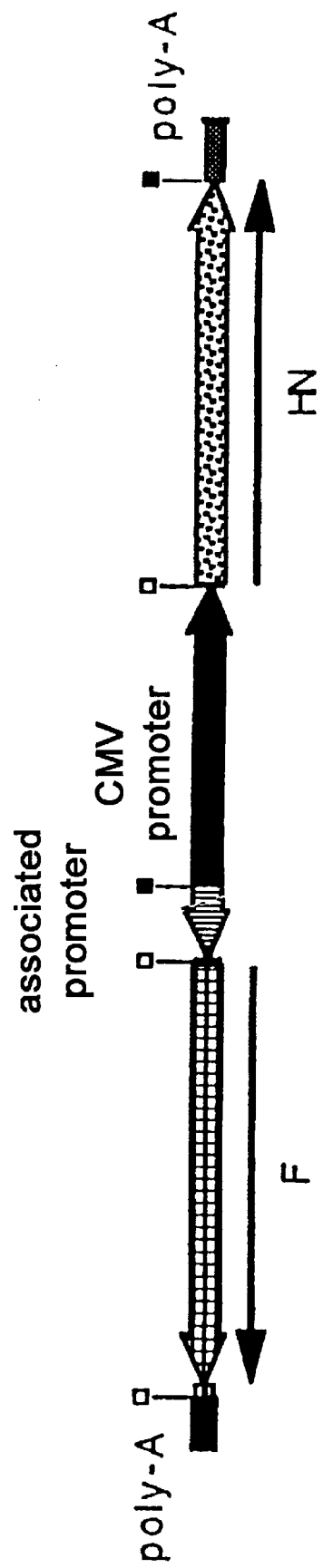

Construction of a Donor Plasmid for the Insertion of a Double Cassette for Expressing the NDV gN and F Genes into the ORF B Site and Isolation of a Recombinant ILTV Virus A double cassette for expressing two genes, for example the NDV virus HN and F genes, may be constructed. Such a construct is schematically represented in FIG. 19. In this construct, the 5' end of the two promoters are adjacent so that the transcription of the two genes occurs in opposite directions. One of the two promoters is preferably a CMV IE promoter and the other promoter (called associated promoter) is any promoter active in eucaryotic cells, of viral (and in particular of herpes virus) origin or otherwise. In this configuration, the associated promoter is activated by the activating region of the CMV IE promoter. This double expression cassette may then be inserted into one of the 3 donor plasmids described above (pMB035, pMB039 and pMB042 described in Examples 6, 7 and 8 and represented in FIGS. 3, 4 and 5 respectively). The isolation of the recombinant viruses is carried out in the same manner as above (see Example 3).

Example 17

Construction of the Donor Plasmid pMB049 for the Insertion of a Cassette for Expressing the MDV gB Gene into the ORF B and Isolation of vILTV7

17.1—Cloning of the Marek's disease virus gB gene

Figure 20:
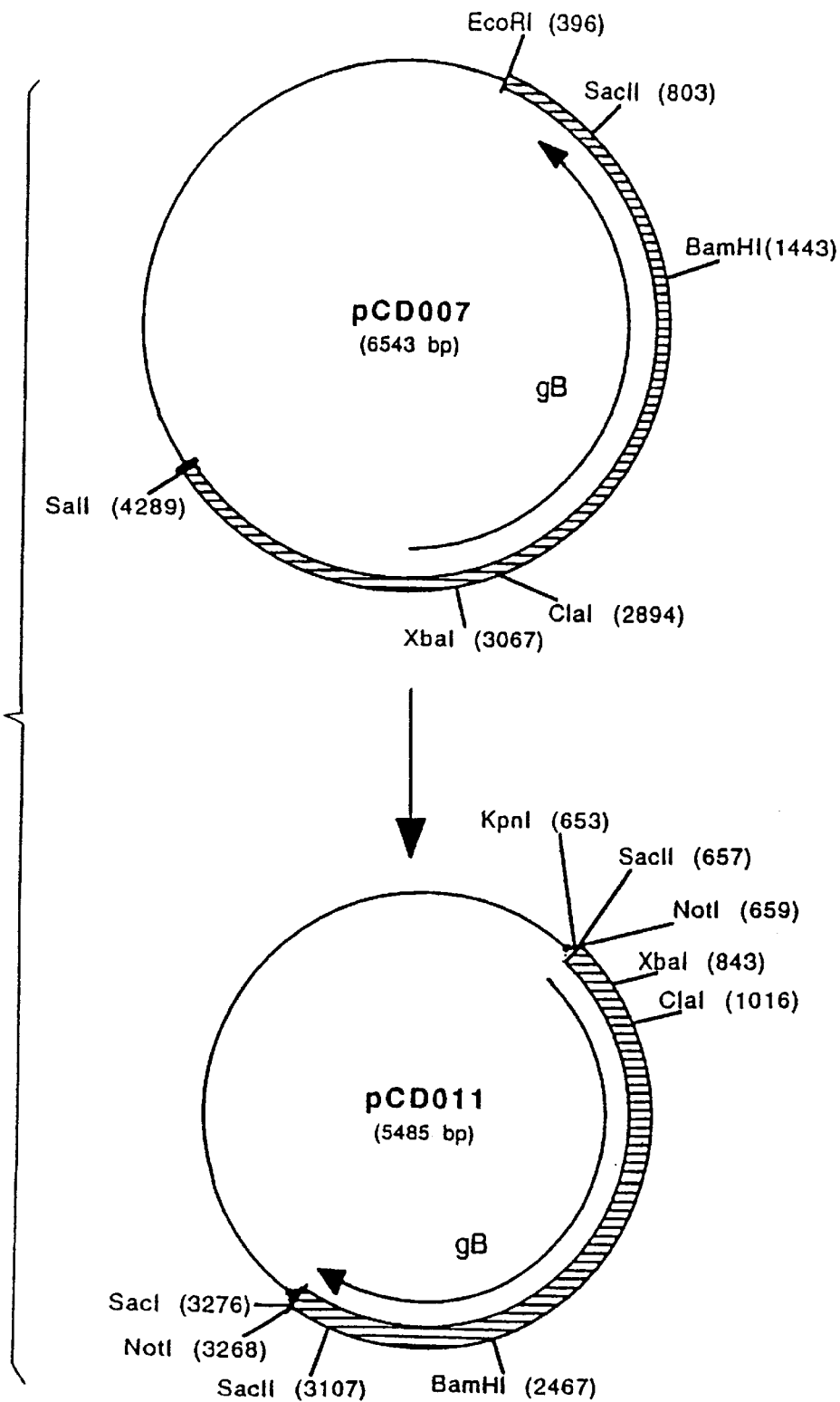

The 3.9 kbp EcoRI-SalI fragment of the genomic DNA from the MDV virus strain RB1B containing the MDV gB gene (sequence published by Ross N. et al. J. Gen. Virol. 1989. 70. 1739–1804) was ligated with the vector pUC13, previously digested with EcoRI and SalI, in order to give the 6543 bp plasmid pCD007 (FIG. 20). This plasmid was digested with SacI and XbaI in order to isolate the 2260 bp SacI-XbaI fragment (central part of the gB gene=fragment A). A PCR was carried out s with the following oligonucleotides:
CD001 (SEQ ID NO:21):
5'GACTGGTACCGCGGCCGCATGCACTT7ITAGGC-bx;1GGAATTG 3'
CD002 (SEQ ID NO:22) 5'TTCGGGACATTTTCGCGG 3'
and the template pCD007 in order to produce a 222 bp PCR fragment. This fragment was digested with KpnI and XbaI in order to isolate a 190 bp KpnI-XbaI fragment (5'end of the gB gene=fragment B). Another PCR was carried out with the following oligonucleotides:
CD002 (SEQ ID NO:23): 5'TATATGGCGTTAGTCTCC 3'
CD004 (SEQ ID NO:24)
5'TTGCGAGCTCGCGGCCGCTTATTACA-CAGCATCATCTTCTG 3'
and the template pCDC07 in order to produce a 195 bp PCR fragment. This fragment was digested with SacI and SacI in order to isolate the 162 bp SacI-SacII fragment (3' end of the gB gene fragment C). The fragments A, B and C were ligated together with the vector pSS-SK+, previously digested with KpnI and SacI, in order to give the 5485 bp plasmid pCD011 (FIG. 20).

Figure 21:
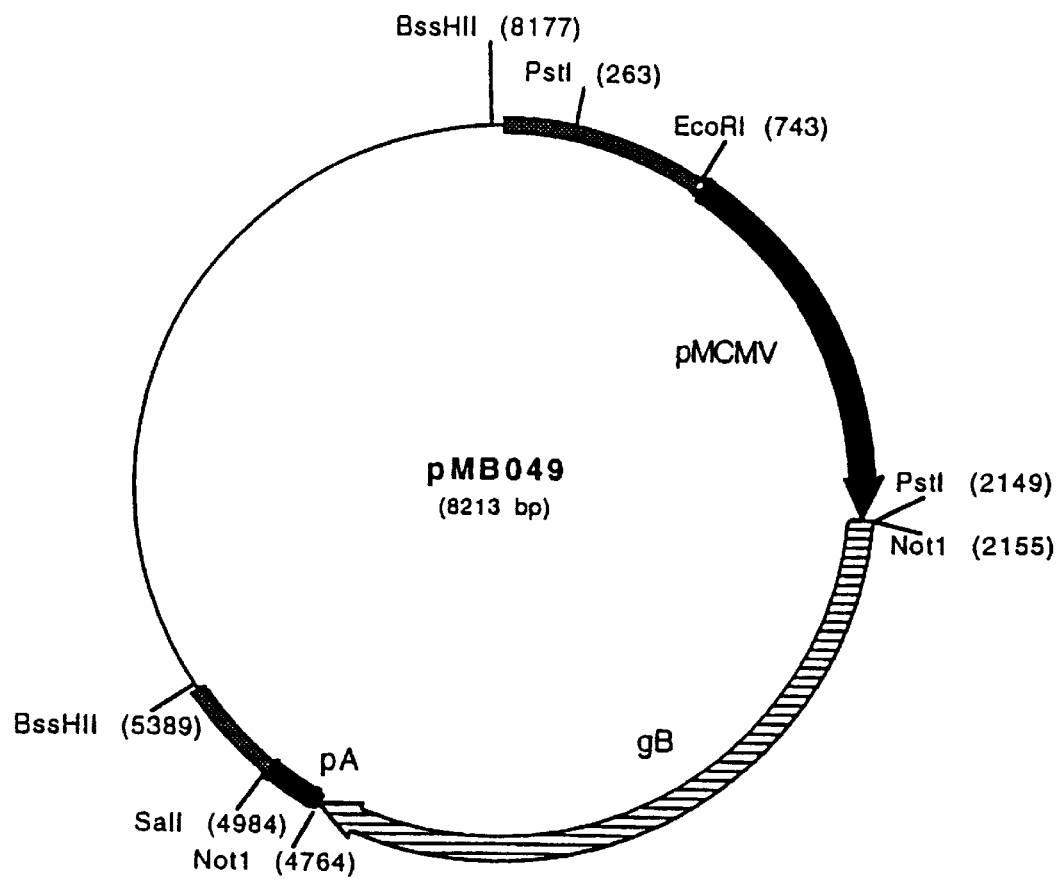

17.2—Construction of the plasmid pM049 containing a cassette for expressing the MDV gB gene in the ORF B The plasmid pCD011 was digested with NotI in order to isolate the 2608 bp NotI-NotI fragment (entire MDV gB gene) . This fragment was inserted into the NotI sites of the plasmid pMB044 (Example 10, FIG. 11) in place of the 1405 bp NotI-NotI fragment containing the gene encoding the IBDV VP2 protein; this cloning made it possible to isolate the 8213 bp plasmid pMB049 (FIG. 21). This plasmid allows the insertion of the expression cassette MCMV-IE/MDV-gB into the partially deleted ORF B of the ILTV virus.

17.3—Isolation and purification of the recombinant virus vILTV7

The vILTV7 virus was isolated and purified after cotransfection of the DNA from the plasmid pMB049 previously linearized with the enzyme BssHII and of the viral DNA, as described in Example 3. This recombinant contains a cassette MCMV-IE/MDV gB in the partially deleted ORF B of the ILTV virus (see Examples S and 6).

Example 18

Construction of a Donor Plasmid for the Insertion of a Cassette for Expressing IBV gene(s) into the ORF B and Isolation of the Recombinant ILTV Virus According to the same strategy as that described above for the insertion of single cassettes (Examples 9, 10, 11, 12, 13, 14, 15 and 17) or for the insertion of double cassettes (Example 18) into the three sites described above (Examples 6, 7 and 8), it is possible to prepare recombinant ILTV viruses expressing, at a high level, the Membrane (M) or Spike (S) proteins, or part of Spike (S1 or S2), or Nucleocapsid (N) of the avian infectious bronchitis virus (IBV). in particular, a double expression cassette was prepared with the S gene under the control of the CMV IE promoter and the M gene under the control of the associated promoter.

Example 19

Construction of Donor Plasmids for the Insertion of Cassettes for Expressing a Gene or Genes of Other Avian Pathogenic Agents or of an Immunomodulatory Peptide into the Three sites Described and Isolation of the Recombinant ILTV Viruses According to the same strategy as that described above for the insertion of single cassettes (Examples 9, 10, 11, 12, 13, 14, 15 and 17) or for the insertion of double cassettes (Example 18) into the three sites described above (Examples 6, 7 and 8), it is possible to prepare recombinant ILTV viruses expressing, at a high level, immunogens from CAV (and especially a double cassette for expressing genes encoding VP1 and VP2), from the chicken pneumovirosis virus, or other avian pathogenic agents, or alternatively immunomodulatory peptides and especially cytokines.

Example 20

Production of Vaccines

The recombinant viruses obtained according to the invention are produced on embryonated eggs. The viral solution harvested is then diluted in a stabilizing solution for freeze-drying, distributed at the rate of 1000 vaccinal doses per vial, and finally freeze-dried.

---

What is claimed is:

1. A recombinant infectious laryngotracheitis virus (ILTV) comprising at least one heterologous nucleotide sequence in an insertion locus, which, in a specific ILTV strain, is defined as between nucleotides 1624 and 3606 in SEQ ID NO: 5.

2. The recombinant ILTV according to claim 1 that expresses at least one heterologous nucleotide sequence.

3. The recombinant ILTV of claim 2 wherein at least one heterologous nucleotide sequence is inserted by simple insertion, or after total or partial deletion of the insertion locus.

4. The recombinant ILTV according to claim 2 wherein at least one heterologous nucleotide sequence is inserted into ORF B between nucleotides 1713 and 2897 in SEQ ID NO: 5.

5. The recombinant ILTV according to claim 2 wherein at least one heterologous nucleotide sequence is inserted into an intergenic region between nucleotides 2898 and 3606 in SEQ ID NO:5.

6. The recombinant ILTV according to claim 2 further comprising a strong eukaryotic promoter; wherein at least one heterologous nucleotide sequence is operably linked to the strong eukaryotic promoter.

7. The recombinant ILTV according to claim 6 wherein the strong eukaryotic promoter is selected from the group consisting of: a CMV immediate-early promoter, the Rous sarcoma virus (RSV) LTR promoter, and the SV40 virus early promoter.

8. The recombinant ILTV of claim 7 wherein the CMV immediate-early promoter comprises a murine or human CMV immediate-early promoter.

9. The recombinant ILTV according to claim 2 comprising at least two heterologous nucleotide sequences inserted into the insertion locus wherein each heterologous nucleotide sequence is under the control of a different eukaryotic promoter.

10. The recombinant ILTV according to claim 9 wherein the eukaryotic promoters are CMV immediate-early promoters of different animal origin.

11. The recombinant ILTV according to claim 9 comprising a first heterologous nucleotide sequence operably linked to a first promoter and a second heterologous nucleotide sequence operably linked to a second promoter; wherein, the first promoter comprises a CMV immediate-early promoter, and, the first and second promoters are arranged so that their 5' ends are adjacent.

12. The recombinant ILTV according to claim 2 wherein at least one heterologous nucleotide sequence comprises a nucleotide sequence encoding an antigenic polypeptide from an avian pathogenic agent.

13. The recombinant ILTV according to claim 12 wherein the avian pathogenic agent is selected from the group consisting of Newcastle disease virus (NDV), infectious bursal disease virus (IBDV), Marek's disease virus (MDV), infectious bronchitis virus (IBV), chicken anaemia virus (CAV), and the chicken pneumovirosis virus.

14. The recombinant ILTV according to claim 13 wherein the at least one heterologous nucleotide sequence comprises a nucleotide sequence selected from group consisting of the nucleotide sequences encoding the NDV F and HN polypeptides.

15. The recombinant ILTV according to claim 13 wherein the at least one heterologous nucleotide sequence comprises a nucleotide sequence selected from the group consisting of nucleotide sequences encoding the MDV gB gD, and gH+gL polypeptides.

16. The recombinant ILTV according to claim 13 wherein the at least one heterologous nucleotide sequence comprises a nucleotide sequence selected from the group consisting of nucleotide sequences encoding the IBDV VP2 antigen, the IBV S antigen, a portion of the IV S antigen, the IBV M antigen, the IBV N antigen, the CAV VP1 antigen, the CAV VP2 antigen, the chicken pneumovirosis virus G antigen, and the chicken pneumovirosis virus F antigen.

17. The recombinant ILTV according to claim 2 wherein at least one heterologous nucleotide sequence comprises a nucleotide sequence encoding an immunomodulatory polypeptide.

18. The recombinant ILTV according to claim 17 wherein the heterologous nucleotide sequence comprises a nucleotide sequence selected from the group consisting of nucleotide sequences encoding cytokines.

19. The recombinant ILTV according to claim 2 wherein the heterologous nucleotide sequence comprises an expression cassette comprising from 5' to 3', a promoter, two or more coding regions separated in pairs by IRES, and a polyadenylation signal.

20. A vaccine or immunological composition comprising a recombinant ILTV as claimed in any one of claims 2 to 19.

21. A multivalent vaccine or immunological composition comprising, as a mixture or to be admixed, at least a first recombinant ILTV and a second recombinant ILTV; wherein the first and second recombinant ILTV are as claimed in any one of claims 2 to 19, and the heterologous nucleotide sequence in the first recombinant ILTV is different than the heterologous nucleotide sequence in the second recombinant ILTV.

22. A method for inducing an immunological response in an animal comprising administering to the avian a recombinant ILTV as claimed in any one of claims 1 to 19.

23. The method of claim 22 wherein the administering comprises in ovo administration.

24. The method of claim 22 wherein the avian is a one-day-old chick.

25. The method of claim 22 wherein the avian is an adult chicken.

26. The method of claim 22 wherein the administering comprises mucosal administration.

27. The method of claim 22 wherein the administering comprises aerosol administration.

28. The method of claim 22 wherein the administering is via drinking water.

29. The method of claim 22 wherein the administering is of a dose between $10^1$–$10^4$ visits per animal.

30. A method for inducing an immunological response in an avian comprising administering to the avian a vaccine or immunological composition as claimed in claim 21.

31. The method of claim 30 wherein the administering comprises in ovo administration.

32. The method of claim 30 wherein the avian is a one-day-old chick.

33. The method of claim 30 wherein the avian is an adult chicken.

34. The method of claim 30 wherein the administering comprises mucosal administration.

35. The method of claim 30 wherein the administering comprises aerosol administration.

36. The method of claim 30 wherein the administering is via drinking water.

37. The method of claim 30 wherein the administering is of a dose between $10^1$–$10^4$ visits per animal.

38. A method for inducing an immunological response in an avian comprising administering to the avian a vaccine or immunological composition as claimed in claim 20.

39. The method of claim 38 wherein the administering comprises in ovo administration.

40. The method of claim 38 wherein the avian is a one-day-old chick.

41. The method of claim 38 wherein the avian is an adult chicken.

42. The method of claim 38 wherein the administering comprises mucosal administration.

43. The method of claim 38 wherein the administering comprises aerosol administration.

44. The method of claim 38 wherein the administering is via drinking water.

45. The method of claim 38 wherein the administering is of a dose between $10^1$–$10^4$ virus per animal.

46. A method for expressing a polypeptide comprising contacting a suitable cell with a recombinant ILTV as claimed in any one of claims 1 to 19.

* * * * *

SEQUENCE LISTING

<160> NUMBER OF SEQ ID NOS: 24

<210> SEQ ID NO 1
<211> LENGTH: 30
<212> TYPE: DNA
<213> ORGANISM: Infectious Laryngotracheitis Virus

<400> SEQUENCE: 1
aagtatactc gaaactagcg cagtactctg                              30

<210> SEQ ID NO 2
<211> LENGTH: 30
<212> TYPE: DNA
<213> ORGANISM: Infectious Laryngotracheitis Virus

<400> SEQUENCE: 2
agatgcgata ccatttttac tgccatttgg                              30

<210> SEQ ID NO 3
<211> LENGTH: 20
<212> TYPE: DNA
<213> ORGANISM: Infectious Laryngotracheitis Virus

<400> SEQUENCE: 3
tcgtgtctct gctatcactg                                         20

<210> SEQ ID NO 4
<211> LENGTH: 20
<212> TYPE: DNA
<213> ORGANISM: Infectious Laryngotracheitis Virus -continued

```
<400> SEQUENCE: 4
agctctccat ggatctagcg                                                      20

<210> SEQ ID NO 5
<211> LENGTH: 3841
<212> TYPE: DNA
<213> ORGANISM: Infectious Laryngotracheitis Virus

<400> SEQUENCE: 5
gtcgactgcc agtggaagat aaatcccctt ctcaattttt aacgataaat gaacactgag         60
tccatggttt cgaataaagc gacgcattcc caagattccc atatcggtat atttcgagga        120
gagcaaatga aaagacagaa gcccgcaagt ctcgtatcag caaactaata tttagggcgc        180
tctgaaaggc ggtatttgta tgtacagggg ttgggcaatc cacaccctcg taatcgcatt        240
acacataagg tgtgacatgg tggtagcccc aaaattttat gcacaggcta cagttgtata        300
taaaccgcgc ggatgtttag gagatgttca gagacaccgg gggagggaac gaacgtacac        360
acgaattacg ttcgttggaa gatggatttg gatactgcga caagaagtaa atgtttgctc        420
cgactaactt taggaaagca tgggatttcg gtggtttccc ccattgccaa aaacatgcgt        480
gggattctgc aacactctgt gctggctttt atgaatgact gcatagtaat ttcctgttcc        540
gctccgtttg ggatggcttt cttaaaaatc aagtggcaat tgttcgactc atttgaatat        600
ttatcagacg atgagagtat actacctatc atgctcaata atactataca ccagcgccct        660
ggagacctct tggattttct gtgggactct aagaaaaaaa ctgtcggaat accaacttta        720
gccacattta ctatatcaga aagtttcaaa tccgatgaaa ctagggctgt acacagactg        780
aaagtctgtc gcgagataga agagagcgcg tcgtgccccc aaaatacgga ataagcacg        840 aaattcaagt actcttcatc ggatggacct cctatatacc tgcctcgttc gataaggca        900 tgtcgggcct cgctggaaca gtattcgttc aatgaaatta caagtggct ttcgaagatc         960 cctaaagata actcaattac agtcacactc acaagagagt atgtcacgtt ctcgtccgca       1020
gaagacgagc aacgcctaac ctttaacgcg aaatggttcg gcgaccagac aagtattgta       1080
tcgtctgcgt caattttgtc tcagctatgt ggccatgaac ctgcgcctaa aaaaagagag       1140
ctctcaagcc gagccatcgg taagaaacta aagaagccc gccattatcg ctgttcatgg        1200
ggacaaagat gcctgcccca ttgtagtatc actctccaga cccggatctc tgaaacagtc       1260
actagggtgg ctgaaaagcg gtccttgggg acaccgtgtc ttacatttta caagactct       1320 gtgaatagtc ttggagtaga actctctgaa agaggaggag aagaattagc tgctgggatt       1380
tttttccttt ccgcgttttc tgcagatgga gcaatctctg agcaatgcca tgatgactca       1440
gacacagcca tgcacgaatt tttggcggag gaggagcgcc tcatacaaca gaccacgcta       1500
tcccattcca actcaagtaa gaagaggtcg ctcgaaaatt acgaggacac cgatattagc       1560
ccatcccacc acccacaaaa gcggggggaaa ttaaagaacg gctcacttgc acggaagaac      1620
taaaatcgtc tcctcgcgtc taccggggag cttagtttac tgccagcgtt tgtgacccaa      1680
gtgtgcaccg tgatttcaac tctaccgcaa ctatgacggg ggctaccata attgatccat       1740
tcgcaccgcc caaggtaaa tggtggccgt tcaatttgaa cgggatagtt ttttccttga        1800
tgatgtttat tatattttta gcctggatac tgcgcattga ctatggactc gcgttagctt       1860
acattacctg ggcaaagctt tctacgaaag aggcaagatt cggatggatg atcggactat       1920
tggtggctac gattactgcc agttttctgg atattcaata ctcggctcac aaaacagtcc       1980
gaatttattt tctggtgatg ctttctatgg cgagcgcagt aataattata tttctcatcc       2040
```

-continued

```
attccaacag ccccaatgcc gcgatagtta tggggctatt ctccgttttt tcggaagttt    2100
gcttgatact gattttggga tttcaactcc gaccggccat tttctgcagc ataaacatga    2160
cctggctctt tcttgaagcc atgctcctaa atttgaccgt actttcttgg aacttgatgc    2220
accttcgagt aaaccctaga tacttggaac cgttggccct ttttactatt aacattttgg    2280
catacaatcc ctctcgtttt ttgctcaaga gtgatttttt taagaccagc atgataactc    2340
tgacgggcag tatagaacca ttttccgaag ataacacgat ttatacaccc caagacaac    2400 ataaagatac tcgcccttca ctgaatgacg gaccaactcg gtggtgcggt tactgtattc    2460
tcgtatctac aacattggtt actgccgctt tcgcctgcac attatcatta ccgttcctgg    2520
gcaaagattt aggtactgta cgcatcggca tgcaaacgaa ttttaaaatc tcatggtag    2580 cgtgcggttc ggttttggca tttggatcta cttgcattgg aaaactatgc aaaatccata    2640
tcgttgtatg gttcgtgata agcatactat taaccttcgt gtctctgcta tcactgatta    2700
agttgattga ggacccagct gacattccat ttggtgtcat tcttgcatcg gtttcttgtc    2760
tgtttcaagt tggagccctc ttttccgag aattaaaaac ggccacccat acacaaggat    2820
ggatttcatg cgcccttctt ttctgctccc ttttcattcc aattgccgcg ccgcttgtgt    2880
gtgagtacaa gctctgaatt cttgtctaag ggagacgtgc caattctgac aacgccctaa    2940
gccaacacaa atgccttcct caatttacgc gctagcttga acattccaac aagatgaatg    3000
catcgctaac atggcttgct ttaacttta aagttacctt gagtttcagc ctgctctgaa    3060
tgttttcctc caaacctaag atgttcttag ttgtacgatt tttgtattgc gaataccaca    3120
tcatccagta ccaaagtact aatggtcggc aatcgaatag aaatcaaaca tggcacgcag    3180
gagactgtcg cctcgaaact gccttcgccg agctgcagaa attcggaacg aggacattag    3240
aaacagatct acattccacc gagcaaccgt ttactggaga aatgctaga gaataaccta    3300 acaggcggcc ttcaactttc actacttaac aactggaact atattgtcga ggattgtcat    3360
agtcacgaac atgatgcagt attgcttcgg atgcaatcta tattttgaca ttgttaataa    3420
agcacatgta ctatgcaaag tttgcattcg tgtaattcgt cgagagagaa agttacaagt    3480
tcgattctct cgcgctagga gtgtttccac gtgcgaaaac gcaaaaattt tcatattatt    3540
cgggcggact gtgtccatag tagctaaatt accgcgatct ggagactagg gcattcacga    3600
ctcaacatgc agcatcagag tactgcgcta gtttcgagta cttttgct cttgagcctg    3660 caaagccttg cgtttgaatt tttctgtgat ccgccacacg ttttcgagg gcagctcggt    3720 gaccccattc tattgcaatg cttcagcgac agacctctaa cccacgaaga atctgtaaaa    3780
gtagaagtaa ttcgacaccc agccagctta gttgaaactg cgctaagcgc ctacgggatc    3840
c                                                                   3841
```

<210> SEQ ID NO 6
<211> LENGTH: 31
<212> TYPE: DNA
<213> ORGANISM: Infectious Laryngotracheitis Virus

<400> SEQUENCE: 6

```
agctgaattc aagcttcccg gggtcgacat g                                  31
```

<210> SEQ ID NO 7
<211> LENGTH: 23
<212> TYPE: DNA
<213> ORGANISM: Infectious Laryngotracheitis Virus

```
<400> SEQUENCE: 7
tcgaccccgg gaagcttgaa ttc                                           23

<210> SEQ ID NO 8
<211> LENGTH: 23
<212> TYPE: DNA
<213> ORGANISM: Infectious Laryngotracheitis Virus

<400> SEQUENCE: 8
gatcgtcgac cccgggaagc ttg                                           23

<210> SEQ ID NO 9
<211> LENGTH: 23
<212> TYPE: DNA
<213> ORGANISM: Infectious Laryngotracheitis Virus

<400> SEQUENCE: 9
aattcaagct tcccggggtc gac                                           23

<210> SEQ ID NO 10
<211> LENGTH: 28
<212> TYPE: DNA
<213> ORGANISM: Infectious Laryngotracheitis Virus

<400> SEQUENCE: 10
agctgaattc aagcttcccg gggtcgac                                      28

<210> SEQ ID NO 11
<211> LENGTH: 28
<212> TYPE: DNA
<213> ORGANISM: Infectious Laryngotracheitis Virus

<400> SEQUENCE: 11
gatcgtcgac cccgggaagc ttgaattc                                      28

<210> SEQ ID NO 12
<211> LENGTH: 50
<212> TYPE: DNA
<213> ORGANISM: Infectious Laryngotracheitis Virus

<400> SEQUENCE: 12
cgaattcact agtgtgtgtc tgcaggcggc cgcgtgtgtg tcgacggtac              50

<210> SEQ ID NO 13
<211> LENGTH: 50
<212> TYPE: DNA
<213> ORGANISM: Infectious Laryngotracheitis Virus

<400> SEQUENCE: 13
cgtcgacaca cacgcggccg cctgcagaca cacactagtg aattcgagct              50

<210> SEQ ID NO 14
<211> LENGTH: 2521
<212> TYPE: DNA
<213> ORGANISM: Infectious Laryngotracheitis Virus

<400> SEQUENCE: 14
tgctacctga tgtacaagca aaaggcacaa caaaagacct tgttatggct tgggaataat    60
acccttgatc agatgagagc cactacaaaa atatgaatac aaacgagagg cggaggtatc   120
cccaatagca atttgcgtgt aaattctggc aacctgttaa ttagaagaat taagaaaaaa   180
ccactggatg taagtgacaa acaagcaata cacgggtaga acgtcggag aagccacccc    240
```

-continued

```
tcaatcggga atcaggcctc acaacgtcct ttctaccgca tcatcaatag cagacttcgg      300
tcatggaccg tgcagttagc agagttgcgc tagagaatga agaaagagaa gcaaagaata      360
catggcgctt tgtattccgg attgcaatct tactttaat agtaacaacc ttagccatct       420
ctgcaaccgc cctggtatat agcatggagg ctagcacgcc tggcgacctt gttggcatac      480
cgactatgat ctctaaggca gaagaaaaga ttacatctgc actcagttct aatcaagatg      540
tagtagatag gatatataag caggtggccc ttgagtctcc attggcgttg ctaaacactg      600
aatctgtaat tatgaatgca ataacgtctc tctcttatca aatcaatgga gctgcaaata      660
atagcgggtg tggggcacct gttcatgacc cagattatat cgggggata ggcaaagaac       720 ttattgtgga tgacgctagt gatgtcacat cattctatcc ctctgcgttc caagaacacc      780
tgaactttat cccggcacct actacaggat caggttgcac tcggataccc tcattcgaca      840
taagcgctac ccactactgt tacactcaca atgtgatatt atctggttgc agagatcact      900
cacactcata tcagtactta gcacttggcg tgcttcggac atctgcaaca gggagggtat      960
tcttttctac tctgcgttcc atcaatttgg atgacagcca aaatcggaag tcttgcagtg     1020
tgagtgcaac tcccttaggt tgtgatatgc tgtgctctaa aatcacagag actgaggaag     1080
aggattatag ttcaattacg cctacatcga tggtgcacgg aaggttaggg tttgacggtc     1140
aataccatga gaaggactta gacgtcataa ctttatttaa ggattgggtg gcaaattacc     1200
caggagtggg gggtgggtct tttattaaca accgcgtatg gttcccagtc tacggagggc     1260
taaaacccaa ttcgcctagt gacaccgcac aagaagggag atatgtaata tacaagcgct     1320
acaatgacac atgcccagat gaacaagatt accagattcg gatggctaag tcttcatata     1380
agcctgggcg gtttggtgga aaacgcgtac agcaggccat cttatctatc aaggtgtcaa     1440
catctttggg cgaggacccg gtgctgactg taccgcctaa tacaatcaca ctcatggggg     1500
ccgaaggcag agttctcaca gtagggacat ctcatttctt gtaccagcga gggtcttcat     1560
acttctctcc tgctttatta taccctatga cagtcaacaa caaaacggct actcttcata     1620
gtccttacac attcaatgct ttcactaggc caggtagtgt cccttgtcag gcatcagcaa     1680
gatgccccaa ctcatgtgtc actggagttt atactgatcc gtatccctta gtcttccata     1740
ggaaccatac cttgcggggg gtattcggga caatgcttga tgatgaacaa gcaagactta     1800
accctgtatc tgcagtattt gataacatat cccgcagtcg cataacccgg gtaagttcaa     1860
gccgtactaa ggcagcatac acgacatcga catgttttaa agttgtcaag accaataaaa     1920
catattgcct cagcattgca gaaatatcca ataccctctt cggggaattc aggatcgttc     1980
ctttactagt tgagattctc aaggatgatg ggatttaaga agcttggtct ggccagttga     2040
gtcaactgcg agagggtcgg aaagatgaca ttgtgtcacc ttttttttgt aatgccaagg     2100
atcaaactgg ataccggcgc gagcccgaat cctatgctgc cagtcagcca taatcagata     2160
gtactaatat gattagtctt aatcttgtcg atagtaactt ggttaagaaa aaatatgagt     2220
ggtagtgaga tacacagcta acaactcac gagagatagc acgggtagga catggcgagc     2280
tccggtcccg aaagggcaga gcatcagatt atcctaccag agtcacatct gtcctcacca     2340
ttggtcaagc acaaactgct ctattactgg aaattaactg gcgtaccgct tcctgacgaa     2400
tgtgacttcg accacctcat tatcagccga caatggaaga aaatacttga atcggccact     2460
cctgacactg agaggatgat aaagctcggg cgggcagtac accagactct cgaccaccgc     2520
c                                                                     2521
```

-continued

```
<210> SEQ ID NO 15
<211> LENGTH: 22
<212> TYPE: DNA
<213> ORGANISM: Infectious Laryngotracheitis Virus

<400> SEQUENCE: 15
cagaccaagc ttcttaaatc cc                                              22

<210> SEQ ID NO 16
<211> LENGTH: 16
<212> TYPE: DNA
<213> ORGANISM: Infectious Laryngotracheitis Virus

<400> SEQUENCE: 16
gtattcggga caatgc                                                     16

<210> SEQ ID NO 17
<211> LENGTH: 21
<212> TYPE: DNA
<213> ORGANISM: Infectious Laryngotracheitis Virus

<400> SEQUENCE: 17
gtgacatcac tagcgtcatc c                                               21

<210> SEQ ID NO 18
<211> LENGTH: 36
<212> TYPE: DNA
<213> ORGANISM: Infectious Laryngotracheitis Virus

<400> SEQUENCE: 18
ccgcatcatc agcggccgcg atcggtcatg gacagt                               36

<210> SEQ ID NO 19
<211> LENGTH: 18
<212> TYPE: DNA
<213> ORGANISM: Infectious Laryngotracheitis Virus

<400> SEQUENCE: 19
tgaccctgtc tgggatga                                                   18

<210> SEQ ID NO 20
<211> LENGTH: 36
<212> TYPE: DNA
<213> ORGANISM: Infectious Laryngotracheitis Virus

<400> SEQUENCE: 20
ggatcccggt cgacacattg cggccgcaag atgggc                               36

<210> SEQ ID NO 21
<211> LENGTH: 40
<212> TYPE: DNA
<213> ORGANISM: Infectious Laryngotracheitis Virus

<400> SEQUENCE: 21
gactggtacc gcggccgcat gcacttttta ggcggaattg                           40

<210> SEQ ID NO 22
<211> LENGTH: 18
<212> TYPE: DNA
<213> ORGANISM: Infectious Laryngotracheitis Virus

<400> SEQUENCE: 22
ttcgggacat tttcgcgg                                                   18
```

-continued

```
<210> SEQ ID NO 23
<211> LENGTH: 18
<212> TYPE: DNA
<213> ORGANISM: Infectious Laryngotracheitis Virus

<400> SEQUENCE: 23
tatatggcgt tagtctcc                                                   18

<210> SEQ ID NO 24
<211> LENGTH: 41
<212> TYPE: DNA
<213> ORGANISM: Infectious Laryngotracheitis Virus

<400> SEQUENCE: 24
ttgcgagctc gcggccgctt attacacagc atcatcttct g                         41
```